United States Patent
Chang et al.

(10) Patent No.: US 11,207,087 B2
(45) Date of Patent: *Dec. 28, 2021

(54) GUIDE SYSTEM WITH SUCTION

(71) Applicant: Acclarent, Inc., Irvine, CA (US)

(72) Inventors: John Y. Chang, Los Altos, CA (US);
Eric Goldfarb, Belmont, CA (US);
Serena Swei Loh, San Carlos, CA (US); Mei Y. Pader, Fremont, CA (US); Michael J. Gottesman, Redwood Shores, CA (US); Richard R. Newhauser, Jr., Redwood City, CA (US)

(73) Assignee: Acclarent, Inc., Irvine, CA (US)

( * ) Notice: Subject to any disclaimer, the term of this patent is extended or adjusted under 35 U.S.C. 154(b) by 200 days.

This patent is subject to a terminal disclaimer.

(21) Appl. No.: 16/523,090

(22) Filed: Jul. 26, 2019

(65) Prior Publication Data
US 2020/0046392 A1  Feb. 13, 2020

Related U.S. Application Data

(60) Continuation of application No. 15/165,209, filed on May 26, 2016, now Pat. No. 10,524,814, which is a
(Continued)

(51) Int. Cl.
*A61B 17/24* (2006.01)
*A61M 25/06* (2006.01)
(Continued)

(52) U.S. Cl.
CPC .......... *A61B 17/24* (2013.01); *A61B 17/3415* (2013.01); *A61B 17/3421* (2013.01);
(Continued)

(58) Field of Classification Search
CPC . A61B 17/24; A61B 17/3421; A61B 17/3415; A61B 1/267; A61B 17/3478;
(Continued)

(56) References Cited

U.S. PATENT DOCUMENTS 446,173 A  12/1891  Maher
504,424 A  9/1893  De Pezzer
(Continued)

FOREIGN PATENT DOCUMENTS

CH  668188  12/1988
CN  2151720  1/1994
(Continued)

OTHER PUBLICATIONS

Argon Medical. Maxxim Medical. Ad for Sniper EliteTM Hydrophilic Ni—Ti Alloy Guidewire (2001).
(Continued)

*Primary Examiner* — Richard G Louis
(74) *Attorney, Agent, or Firm* — Frost Brown Todd LLC

(57) ABSTRACT

A guide catheter for use in treating sinuses, the catheter including a catheter shaft configured to provide suction about a balloon catheter and a distal portion shaped for navigating body anatomy. In one embodiment, the guide catheter includes a valve for sealing the balloon catheter and a vent for controlling suction.

20 Claims, 27 Drawing Sheets

Related U.S. Application Data division of application No. 12/408,524, filed on Mar. 20, 2009, now abandoned.

(51) Int. Cl.
| | |
|---|---|
| *A61M 25/09* | (2006.01) |
| *A61M 29/02* | (2006.01) |
| *A61M 25/00* | (2006.01) |
| *A61B 17/34* | (2006.01) |
| *A61B 17/00* | (2006.01) |
| *A61B 1/267* | (2006.01) |

(52) U.S. Cl.
CPC ...... *A61M 25/008* (2013.01); *A61M 25/0041* (2013.01); *A61M 25/0054* (2013.01); *A61M 25/0068* (2013.01); *A61M 25/0097* (2013.01); *A61M 25/0662* (2013.01); *A61M 25/09* (2013.01); *A61M 29/02* (2013.01); *A61B 1/267* (2013.01); *A61B 17/3478* (2013.01); *A61B 2017/00738* (2013.01); *A61B 2017/246* (2013.01); *A61B 2017/345* (2013.01); *A61B 2017/346* (2013.01); *A61B 2217/005* (2013.01); *A61M 25/0074* (2013.01); *A61M 25/0082* (2013.01); *A61M 2210/0681* (2013.01)

(58) Field of Classification Search
CPC ........ A61B 2017/246; A61B 2017/345; A61B 2217/005; A61B 2017/00738; A61B 2017/346; A61M 25/0097; A61M 25/0068; A61M 25/0054; A61M 25/0041; A61M 25/008; A61M 25/0662; A61M 25/09; A61M 29/02; A61M 25/0074; A61M 25/0082; A61M 2210/0681

See application file for complete search history.

(56) References Cited

U.S. PATENT DOCUMENTS

| | | |
|---|---|---|
| 513,667 A | 1/1894 | Buckingham |
| 705,346 A | 7/1902 | Hamilton |
| 798,775 A | 9/1905 | Forsyte |
| 816,792 A | 4/1906 | Green |
| 1,080,934 A | 12/1913 | Shackleford |
| 1,200,267 A | 10/1916 | Sunnergren |
| 1,650,959 A | 11/1927 | Pitman |
| 1,735,519 A | 11/1929 | Vance |
| 1,828,986 A | 10/1931 | Stevens |
| 2,201,749 A | 5/1940 | Vandegrift |
| 2,493,326 A | 1/1950 | Trinder |
| 2,525,183 A | 10/1950 | Robison |
| 2,847,997 A | 8/1958 | Tibone |
| 2,899,227 A | 8/1959 | Jeanrenaud |
| 2,906,179 A | 9/1959 | Bower |
| 2,995,832 A | 8/1961 | Alderson |
| 3,009,265 A | 11/1961 | Bexark |
| 3,037,286 A | 6/1962 | Bower |
| 3,173,418 A | 3/1965 | baran |
| 3,347,061 A | 10/1967 | Stuemky |
| 3,376,659 A | 4/1968 | Asin et al. |
| 3,384,970 A | 5/1968 | Avalear |
| 3,393,073 A | 7/1968 | Reutenauer et al. |
| 3,435,826 A | 4/1969 | Fogarty |
| 3,469,578 A | 9/1969 | Bierman |
| 3,469,582 A | 9/1969 | Jackson |
| 3,481,043 A | 12/1969 | Esch |
| 3,486,539 A | 12/1969 | Jacuzzi |
| 3,506,005 A | 4/1970 | Gilio et al. |
| 3,509,638 A | 5/1970 | Macleod |
| 3,515,888 A | 6/1970 | Lewis |
| 3,527,220 A | 9/1970 | Summers |
| 3,531,868 A | 10/1970 | Stevenson |
| 3,552,384 A | 1/1971 | Pierie et al. |
| 3,595,234 A | 7/1971 | Jackson |
| 3,624,661 A | 11/1971 | Shebanow |
| 3,731,963 A | 5/1973 | Pond |
| 3,792,391 A | 2/1974 | Ewing |
| 3,800,788 A | 4/1974 | White |
| 3,802,096 A | 4/1974 | Matern |
| 3,804,081 A | 4/1974 | Kinoshita |
| 3,834,394 A | 9/1974 | Hunter et al. |
| 3,850,176 A | 11/1974 | Gottschalk |
| 3,856,000 A | 12/1974 | Chikama |
| 3,859,993 A | 1/1975 | Bitner |
| 3,871,365 A | 3/1975 | Chikama |
| 3,894,538 A | 7/1975 | Richter |
| 3,903,893 A | 9/1975 | Scheer |
| 3,910,617 A | 10/1975 | Scalza et al. |
| 3,921,636 A | 11/1975 | Zaffaroni |
| 3,948,254 A | 4/1976 | Zaffaroni |
| 3,948,262 A | 4/1976 | Zaffaroni |
| 3,967,618 A | 7/1976 | Zaffaroni |
| 3,993,069 A | 11/1976 | Buckles et al. |
| 3,993,072 A | 11/1976 | Zaffaroni |
| 3,993,073 A | 11/1976 | Zaffaroni |
| 4,016,251 A | 4/1977 | Higuchi et al. |
| 4,052,505 A | 10/1977 | Higuchi et al. |
| 4,053,975 A | 10/1977 | Olbrich et al. |
| 4,069,307 A | 1/1978 | Higuchi et al. |
| 4,102,342 A | 7/1978 | Akiyama et al. |
| 4,138,151 A | 2/1979 | Nakao |
| 4,184,497 A | 1/1980 | Kolff et al. |
| 4,198,766 A | 4/1980 | Camin et al. |
| 4,207,890 A | 6/1980 | Mamajek et al. |
| 4,209,919 A | 7/1980 | Kirikae et al. |
| 4,213,095 A | 7/1980 | Falconer |
| 4,217,898 A | 8/1980 | Theeuwes |
| 4,268,115 A | 5/1981 | Slemon et al. |
| 4,287,889 A | 9/1981 | Stupar |
| 4,299,226 A | 11/1981 | Banka |
| 4,299,227 A | 11/1981 | Lincoff |
| 4,338,941 A | 7/1982 | Payton |
| D269,204 S | 5/1983 | Trepp |
| 4,388,941 A | 6/1983 | Reidhammer |
| RE31,351 E | 8/1983 | Falconer |
| 4,435,716 A | 3/1984 | Zandbergen |
| 4,437,856 A | 3/1984 | Valli |
| 4,450,150 A | 5/1984 | Sidman |
| 4,459,977 A | 7/1984 | Pizon et al. |
| 4,464,175 A | 8/1984 | Altman et al. |
| 4,471,779 A | 9/1984 | Antoshkiw et al. |
| 4,499,899 A | 2/1985 | Lyons, III |
| 4,554,929 A | 11/1985 | Samson et al. |
| 4,564,364 A | 1/1986 | Zaffaroni et al. |
| 4,571,239 A | 2/1986 | Heyman |
| 4,571,240 A | 2/1986 | Samson et al. |
| 4,581,017 A | 4/1986 | Sahota |
| 4,585,000 A | 4/1986 | Hershenson |
| D283,921 S | 5/1986 | Dyak |
| 4,589,868 A | 5/1986 | Dretler |
| 4,596,528 A | 6/1986 | Lewis et al. |
| D284,892 S | 7/1986 | Glassman |
| 4,603,564 A | 8/1986 | Kleinhany et al. |
| 4,606,346 A | 8/1986 | Berg et al. |
| 4,607,622 A | 8/1986 | Fritch et al. |
| 4,637,389 A | 1/1987 | Heyden |
| 4,639,244 A | 1/1987 | Rizk et al. |
| 4,645,495 A | 2/1987 | Vaillancourt |
| 4,669,469 A | 6/1987 | Gifford, III |
| 4,672,961 A | 6/1987 | Davies |
| 4,675,613 A | 6/1987 | Naegeli et al. |
| 4,691,948 A | 9/1987 | Austin, Jr. et al. |
| 4,708,434 A | 11/1987 | Tsuno |
| 4,708,834 A | 11/1987 | Cohen et al. |
| 4,726,772 A | 2/1988 | Amplatz |
| 4,736,970 A | 4/1988 | McGourty et al. |
| 4,737,141 A | 4/1988 | Spits |
| 4,748,869 A | 6/1988 | Ohtsuka |
| 4,748,969 A | 6/1988 | Wardle |
| 4,748,986 A | 6/1988 | Morrison et al. |
| 4,755,171 A | 7/1988 | Tennant |

(56) References Cited

U.S. PATENT DOCUMENTS

| | | |
|---|---|---|
| 4,771,776 A | 9/1988 | Powell et al. |
| 4,793,359 A | 12/1988 | Sharrow |
| 4,796,629 A | 1/1989 | Grayzel |
| 4,803,076 A | 2/1989 | Ranade |
| 4,811,743 A | 3/1989 | Stevens |
| 4,815,478 A | 3/1989 | Buchbinder et al. |
| 4,819,619 A | 4/1989 | Augustine et al. |
| 4,846,186 A | 7/1989 | Box et al. |
| 4,847,258 A | 7/1989 | Sturm et al. |
| 4,851,228 A | 7/1989 | Zenter et al. |
| 4,854,330 A | 8/1989 | Evans, III et al. |
| 4,862,874 A | 9/1989 | Kellner |
| 4,867,138 A | 9/1989 | Kubota et al. |
| 4,883,465 A | 11/1989 | Brennan |
| 4,897,651 A | 1/1990 | DeMonte |
| 4,898,577 A | 2/1990 | Badger et al. |
| 4,917,419 A | 4/1990 | Mora, Jr. et al. |
| 4,917,667 A | 4/1990 | Jackson |
| 4,919,112 A | 4/1990 | Siegmund |
| 4,920,967 A | 5/1990 | Cottonaro et al. |
| 4,925,445 A | 5/1990 | Sakamoto et al. |
| 4,940,062 A | 7/1990 | Hampton et al. |
| 4,943,275 A | 7/1990 | Stricker |
| 4,946,466 A | 8/1990 | Pinchuk et al. |
| 4,961,433 A | 10/1990 | Christian |
| 4,966,163 A | 10/1990 | Kraus et al. |
| 4,984,581 A | 1/1991 | Stice |
| 4,994,033 A | 2/1991 | Shockey et al. |
| 4,998,916 A | 3/1991 | Hammerslag et al. |
| 4,998,917 A | 3/1991 | Gaiser et al. |
| 5,001,825 A | 3/1991 | Halpern |
| 5,002,322 A | 3/1991 | Fukumoto |
| 5,019,075 A | 5/1991 | Spears et al. |
| 5,019,372 A | 5/1991 | Folkman et al. |
| 5,020,514 A | 6/1991 | Heckele |
| 5,021,043 A | 6/1991 | Becker et al. |
| 5,024,650 A | 6/1991 | Hagiwara et al. |
| 5,024,658 A | 6/1991 | Kozlov et al. |
| 5,026,384 A | 6/1991 | Farr et al. |
| 5,030,227 A | 7/1991 | Rosenbluth et al. |
| 5,041,089 A | 8/1991 | Mueller et al. |
| 5,044,678 A | 9/1991 | Detweiler |
| 5,053,007 A | 10/1991 | Euteneuer |
| 5,055,051 A | 10/1991 | Duncan |
| 5,060,660 A | 10/1991 | Gamble et al. |
| 5,067,489 A | 11/1991 | Lind |
| 5,069,226 A | 12/1991 | Tamauchi et al. |
| 5,083,561 A | 1/1992 | Russo |
| 5,087,244 A | 2/1992 | Wolinsky et al. |
| 5,087,246 A | 2/1992 | Smith |
| 5,090,595 A | 2/1992 | Vandeninck |
| 5,090,910 A | 2/1992 | Narlo |
| 5,112,228 A | 5/1992 | Zouras |
| 5,116,311 A | 5/1992 | Lofstedt |
| 5,127,393 A | 7/1992 | McFarlin et al. |
| 5,127,626 A | 7/1992 | Hilal et al. |
| 5,137,517 A | 8/1992 | Loney et al. |
| 5,139,510 A | 8/1992 | Goldsmith, III et al. |
| 5,139,832 A | 8/1992 | Hayashi et al. |
| D329,496 S | 9/1992 | Wotton |
| 5,152,747 A | 10/1992 | Oliver |
| 5,156,595 A | 10/1992 | Adams |
| 5,163,989 A | 11/1992 | Campbell et al. |
| 5,167,220 A | 12/1992 | Brown |
| 5,168,864 A | 12/1992 | Skockey |
| 5,169,386 A | 12/1992 | Becker et al. |
| 5,171,233 A | 12/1992 | Amplatz et al. |
| 5,180,368 A | 1/1993 | Garrison |
| 5,183,470 A | 2/1993 | Wettermann |
| 5,189,110 A | 2/1993 | Ikematu et al. |
| 5,195,168 A | 3/1993 | Yong |
| 5,196,043 A | 3/1993 | Wurtz |
| 5,197,457 A | 3/1993 | Adair |
| 5,207,695 A | 5/1993 | Trout, III |
| 5,211,952 A | 5/1993 | Spicer et al. |
| 5,215,105 A | 6/1993 | Kizelshteyn et al. |
| 5,221,260 A | 6/1993 | Burns et al. |
| 5,226,302 A | 7/1993 | Anderson |
| 5,230,348 A | 7/1993 | Ishibe et al. |
| 5,236,422 A | 8/1993 | Eplett, Jr. |
| 5,243,996 A | 9/1993 | Hall |
| D340,111 S | 10/1993 | Yoshikawa |
| 5,250,059 A | 10/1993 | Andreas et al. |
| 5,251,092 A | 10/1993 | Brady et al. |
| 5,252,183 A | 10/1993 | Shaban et al. |
| 5,255,679 A | 10/1993 | Imran |
| 5,263,926 A | 11/1993 | Wilk |
| 5,264,260 A | 11/1993 | Saab |
| 5,267,965 A | 12/1993 | Deneiga |
| 5,270,086 A | 12/1993 | Hamlin |
| 5,273,052 A | 12/1993 | Kraus et al. |
| 5,275,593 A | 1/1994 | Easley et al. |
| 5,286,254 A | 2/1994 | Shapland et al. |
| 5,295,694 A | 3/1994 | Levin |
| 5,300,085 A | 4/1994 | Yock |
| 5,304,123 A | 4/1994 | Atala et al. |
| 5,308,326 A | 5/1994 | Zimmon |
| 5,313,967 A | 5/1994 | Lieber et al. |
| 5,314,417 A | 5/1994 | Stephens et al. |
| 5,315,618 A | 5/1994 | Yoshida |
| 5,333,620 A | 8/1994 | Moutafis et al. |
| 5,334,167 A | 8/1994 | Cocanower |
| 5,336,163 A | 8/1994 | DeMane et al. |
| 5,341,818 A | 8/1994 | Abrams et al. |
| 5,342,296 A | 8/1994 | Persson et al. |
| 5,343,865 A | 9/1994 | Gardineer et al. |
| 5,345,945 A | 9/1994 | Hodgson et al. |
| 5,346,075 A | 9/1994 | Nichols et al. |
| 5,346,508 A | 9/1994 | Hastings |
| 5,348,537 A | 9/1994 | Wiesner et al. |
| 5,350,396 A | 9/1994 | Eliachar |
| 5,356,418 A | 10/1994 | Shturman |
| 5,368,049 A | 11/1994 | Raman et al. |
| 5,368,566 A | 11/1994 | Crocker |
| 5,372,138 A | 12/1994 | Crowley et al. |
| 5,372,584 A | 12/1994 | Zink et al. |
| D355,031 S | 1/1995 | Yoshikawa |
| 5,386,817 A | 2/1995 | Jones |
| 5,391,147 A | 2/1995 | Imran et al. |
| 5,391,179 A | 2/1995 | Mezzoli |
| 5,402,799 A | 4/1995 | Colon et al. |
| 5,409,444 A | 4/1995 | Kensey |
| 5,411,475 A | 5/1995 | Atala et al. |
| 5,411,476 A | 5/1995 | Abrams et al. |
| 5,411,477 A | 5/1995 | Saab |
| 5,415,633 A | 5/1995 | Lazarus |
| 5,425,370 A | 6/1995 | Vilkomerson |
| 5,439,446 A | 8/1995 | Barry |
| 5,441,494 A | 8/1995 | Ortiz |
| 5,441,497 A | 8/1995 | Narciso, Jr. |
| 5,447,503 A | 9/1995 | Miller |
| 5,450,853 A | 9/1995 | Hastings et al. |
| 5,451,221 A | 9/1995 | Cho et al. |
| 5,454,817 A | 10/1995 | Katz |
| 5,458,572 A | 10/1995 | Campbell et al. |
| 5,465,717 A | 11/1995 | Imran et al. |
| 5,465,733 A | 11/1995 | Hinohara et al. |
| 5,478,565 A | 12/1995 | Geria |
| 5,486,181 A | 1/1996 | Cohen et al. |
| 5,496,338 A | 3/1996 | Miyagi et al. |
| 5,497,783 A | 3/1996 | Urick et al. |
| 5,507,301 A | 4/1996 | Wasicek et al. |
| 5,507,725 A | 4/1996 | Savage et al. |
| 5,507,766 A | 4/1996 | Kugo et al. |
| 5,512,055 A | 4/1996 | Domb et al. |
| 5,514,128 A | 5/1996 | Hillsman et al. |
| 5,519,532 A | 5/1996 | Broome |
| 5,527,292 A | 6/1996 | Adams et al. |
| 5,531,676 A | 7/1996 | Edwards et al. |
| 5,533,985 A | 7/1996 | Wong |
| 5,538,008 A | 7/1996 | Crowe |
| 5,546,964 A | 8/1996 | Stangerup |
| 5,549,542 A | 8/1996 | Kovalcheck |
| 5,558,073 A | 9/1996 | Pomeranz et al. |

(56) References Cited

U.S. PATENT DOCUMENTS

| | | |
|---|---|---|
| 5,558,652 A | 9/1996 | Henke |
| 5,562,619 A | 10/1996 | Mirarchi et al. |
| 5,568,809 A | 10/1996 | Ben-Haim |
| 5,578,007 A | 11/1996 | Imran |
| 5,578,048 A | 11/1996 | Pasqualucci et al. |
| 5,584,827 A | 12/1996 | Korteweg et al. |
| 5,591,194 A | 1/1997 | Berthiaume |
| 5,599,284 A | 2/1997 | Shea |
| 5,599,304 A | 2/1997 | Shaari |
| 5,599,576 A | 2/1997 | Opolski |
| 5,601,087 A | 2/1997 | Gunderson et al. |
| 5,601,594 A | 2/1997 | Best |
| 5,603,698 A | 2/1997 | Roberts et al. |
| 5,607,386 A | 3/1997 | Flam |
| 5,617,870 A | 4/1997 | Hastings et al. |
| 5,626,374 A | 5/1997 | Kim |
| 5,633,000 A | 5/1997 | Grossman et al. |
| 5,634,908 A | 6/1997 | Loomas |
| 5,638,819 A | 6/1997 | Manwaring et al. |
| 5,643,251 A | 7/1997 | Hillsman et al. |
| 5,645,789 A | 7/1997 | Roucher, Jr. |
| 5,647,361 A | 7/1997 | Damadian |
| 5,656,030 A | 8/1997 | Hunjan et al. |
| 5,662,674 A | 9/1997 | Debbas |
| 5,664,567 A | 9/1997 | Linder |
| 5,664,580 A | 9/1997 | Erickson et al. |
| 5,665,052 A | 9/1997 | Bullard |
| 5,669,388 A | 9/1997 | Vilkomerson |
| 5,673,707 A | 10/1997 | Chandrasekaran |
| 5,676,673 A | 10/1997 | Ferre et al. |
| 5,679,400 A | 10/1997 | Tuch |
| 5,682,199 A | 10/1997 | Lankford |
| 5,685,838 A | 11/1997 | Peters et al. |
| 5,685,847 A | 11/1997 | Barry |
| 5,690,373 A | 11/1997 | Luker |
| 5,693,065 A | 12/1997 | Rains, III |
| 5,694,945 A | 12/1997 | Ben-Haim |
| 5,697,159 A | 12/1997 | Linden |
| 5,700,286 A | 12/1997 | Tartaglia et al. |
| 5,707,389 A | 1/1998 | Louw et al. |
| 5,708,175 A | 1/1998 | Loyanagi et al. |
| 5,711,315 A | 1/1998 | Jerusalmy |
| 5,713,839 A | 2/1998 | Shea |
| 5,713,946 A | 2/1998 | Ben-Haim |
| 5,718,702 A | 2/1998 | Edwards |
| 5,720,300 A | 2/1998 | Fagan et al. |
| 5,722,401 A | 3/1998 | Pietroski et al. |
| 5,722,415 A | 3/1998 | Rom et al. |
| 5,722,984 A | 3/1998 | Fischell et al. |
| 5,729,129 A | 3/1998 | Acker |
| 5,730,128 A | 3/1998 | Pomeranz et al. |
| 5,733,248 A | 3/1998 | Adams et al. |
| 5,752,513 A | 5/1998 | Acker et al. |
| 5,762,604 A | 6/1998 | Kieturakis |
| 5,766,158 A | 6/1998 | Opolski |
| 5,775,327 A | 7/1998 | Randolph et al. |
| 5,776,158 A | 7/1998 | Chou |
| 5,779,699 A | 7/1998 | Lipson |
| 5,789,391 A | 8/1998 | Jacobus et al. |
| 5,792,100 A | 8/1998 | Shantha |
| 5,797,878 A | 8/1998 | Bleam |
| 5,803,089 A | 9/1998 | Ferre et al. |
| 5,814,016 A | 9/1998 | Valley et al. |
| 5,819,723 A | 10/1998 | Joseph |
| 5,820,568 A | 10/1998 | Willis |
| 5,824,044 A | 10/1998 | Quiachon et al. |
| 5,824,048 A | 10/1998 | Tuch |
| 5,824,173 A | 10/1998 | Fontirroche et al. |
| 5,827,224 A | 10/1998 | Shippert |
| 5,830,188 A | 11/1998 | Abouleish |
| 5,833,608 A | 11/1998 | Acker |
| 5,833,645 A | 11/1998 | Lieber et al. |
| 5,833,650 A | 11/1998 | Imran |
| 5,833,682 A | 11/1998 | Amplatz et al. |
| 5,836,638 A | 11/1998 | Slocum |
| 5,836,935 A | 11/1998 | Ashton et al. |
| 5,837,313 A | 11/1998 | Ding et al. |
| 5,843,089 A | 12/1998 | Shatjian et al. |
| 5,843,113 A | 12/1998 | High |
| 5,846,259 A | 12/1998 | Berthiaume |
| 5,857,998 A | 1/1999 | Barry |
| 5,862,693 A | 1/1999 | Myers et al. |
| 5,865,767 A | 2/1999 | Frechette et al. |
| 5,872,879 A | 2/1999 | Hamm |
| 5,873,835 A | 2/1999 | Hastings |
| 5,887,467 A | 3/1999 | Butterweck et al. |
| 5,902,247 A | 5/1999 | Coe et al. |
| 5,902,333 A | 5/1999 | Roberts et al. |
| 5,904,701 A | 5/1999 | Daneshvar |
| 5,908,407 A | 6/1999 | Frazee et al. |
| 5,916,193 A | 6/1999 | Stevens et al. |
| 5,928,192 A | 7/1999 | Maahs |
| 5,931,811 A | 8/1999 | Haissaguerre et al. |
| 5,931,818 A | 8/1999 | Werp et al. |
| 5,932,035 A | 8/1999 | Koger et al. |
| 5,935,061 A | 8/1999 | Acker et al. |
| 5,941,816 A | 8/1999 | Barthel et al. |
| D413,629 S | 9/1999 | Wolff et al. |
| 5,947,988 A | 9/1999 | Smith |
| 5,949,929 A | 9/1999 | Hamm |
| 5,954,693 A | 9/1999 | Barry |
| 5,954,694 A | 9/1999 | Sunseri |
| 5,957,842 A | 9/1999 | Littmann et al. |
| 5,968,085 A | 10/1999 | Morris et al. |
| 5,971,975 A | 10/1999 | Mills et al. |
| 5,979,290 A | 11/1999 | Simeone |
| 5,980,503 A | 11/1999 | Chin |
| 5,980,551 A | 11/1999 | Summers et al. |
| 5,984,945 A | 11/1999 | Sirhan |
| 5,985,307 A | 11/1999 | Hanson et al. |
| 5,997,562 A | 12/1999 | Zadno-Azizi et al. |
| 6,006,126 A | 12/1999 | Cosman |
| 6,006,130 A | 12/1999 | Higo et al. |
| 6,007,516 A | 12/1999 | Burbank et al. |
| 6,007,991 A | 12/1999 | Sivaraman et al. |
| 6,010,511 A | 1/2000 | Murphy |
| 6,013,019 A | 1/2000 | Fischell et al. |
| 6,015,414 A | 1/2000 | Werp et al. |
| 6,016,429 A | 1/2000 | Khafizov et al. |
| 6,016,439 A | 1/2000 | Acker |
| 6,019,736 A | 2/2000 | Avellanet et al. |
| 6,019,777 A | 2/2000 | Mackenzie |
| 6,021,340 A | 2/2000 | Randolph et al. |
| 6,022,313 A | 2/2000 | Ginn et al. |
| 6,027,461 A | 2/2000 | Walker et al. |
| 6,027,478 A | 2/2000 | Katz |
| 6,039,699 A | 3/2000 | Viera |
| 6,042,561 A | 3/2000 | Ash et al. |
| 6,045,531 A | 4/2000 | Davis |
| 6,048,299 A | 4/2000 | von Hoffmann |
| 6,048,358 A | 4/2000 | Barak |
| 6,053,172 A | 4/2000 | Hovda et al. |
| 6,056,702 A | 5/2000 | Lorenzo |
| 6,059,752 A | 5/2000 | Segal |
| 6,071,233 A | 6/2000 | Ishikawa et al. |
| 6,079,755 A | 6/2000 | Chang |
| 6,080,190 A | 6/2000 | Schwartz |
| 6,083,148 A | 7/2000 | Williams |
| 6,083,188 A | 7/2000 | Becker et al. |
| 6,086,585 A | 7/2000 | Hovda et al. |
| 6,092,846 A | 7/2000 | Fuss et al. |
| 6,093,150 A | 7/2000 | Chandler et al. |
| 6,093,195 A | 7/2000 | Ouchi |
| 6,109,268 A | 8/2000 | Thapliyal et al. |
| 6,113,567 A | 9/2000 | Becker |
| 6,122,541 A | 9/2000 | Cosman et al. |
| 6,123,697 A | 9/2000 | Shippert |
| 6,136,006 A | 10/2000 | Johnson et al. |
| 6,139,510 A | 10/2000 | Palermo |
| 6,142,957 A | 11/2000 | Diamond et al. |
| 6,148,823 A | 11/2000 | Hastings |
| 6,149,213 A | 11/2000 | Sokurenko et al. |
| 6,159,170 A | 12/2000 | Borodulin et al. |
| 6,171,298 B1 | 1/2001 | Matsuura et al. |

(56) References Cited

U.S. PATENT DOCUMENTS

| | | |
|---|---|---|
| 6,171,303 B1 | 1/2001 | Ben-Haim |
| 6,174,280 B1 | 1/2001 | Oneda et al. |
| 6,176,829 B1 | 1/2001 | Vilkomerson |
| 6,183,433 B1 | 2/2001 | Bays |
| 6,183,461 B1 | 2/2001 | Matsuura et al. |
| 6,183,464 B1 | 2/2001 | Sharp et al. |
| 6,190,353 B1 | 2/2001 | Makower et al. |
| 6,190,381 B1 | 2/2001 | Olsen et al. |
| 6,193,650 B1 | 2/2001 | Ryan, Jr. |
| 6,195,225 B1 | 2/2001 | Komatsu et al. |
| 6,200,257 B1 | 3/2001 | Winkler |
| 6,206,868 B1 * | 3/2001 | Parodi .................. A61B 17/12 604/500 |
| 6,206,870 B1 | 3/2001 | Kanner |
| 6,213,975 B1 | 4/2001 | Laksin |
| 6,221,042 B1 | 4/2001 | Adams |
| 6,231,543 B1 | 5/2001 | Hegde et al. |
| 6,234,958 B1 | 5/2001 | Snoke et al. |
| 6,238,364 B1 | 5/2001 | Becker |
| 6,238,391 B1 | 5/2001 | Olsen et al. |
| 6,241,519 B1 | 6/2001 | Sedleemayer |
| 6,249,180 B1 | 6/2001 | Maalej et al. |
| 6,254,550 B1 | 7/2001 | McNamara et al. |
| 6,268,574 B1 | 7/2001 | Edens |
| 6,293,957 B1 | 9/2001 | Peters et al. |
| 6,302,875 B1 | 10/2001 | Makower et al. |
| 6,306,105 B1 | 10/2001 | Rooney et al. |
| 6,306,124 B1 | 10/2001 | Jones et al. |
| D450,382 S | 11/2001 | Nestenborg |
| 6,322,495 B1 | 11/2001 | Snow et al. |
| 6,328,564 B1 | 12/2001 | Thurow |
| 6,332,089 B1 | 12/2001 | Acker et al. |
| 6,332,891 B1 | 12/2001 | Himes |
| 6,340,360 B1 | 1/2002 | Lyles et al. |
| 6,348,041 B1 | 2/2002 | Klint |
| 6,352,503 B1 | 3/2002 | Matsui et al. |
| 6,375,615 B1 | 4/2002 | Flaherty et al. |
| 6,375,629 B1 | 4/2002 | Muni et al. |
| 6,379,329 B1 | 4/2002 | Naglreiter et al. |
| 6,383,146 B1 | 5/2002 | Klint |
| 6,386,197 B1 | 5/2002 | Miller |
| 6,389,313 B1 | 5/2002 | Marchitto et al. |
| 6,390,993 B1 | 5/2002 | Cornish et al. |
| 6,394,093 B1 | 5/2002 | Lethi |
| 6,398,758 B1 | 6/2002 | Jacobsen et al. |
| 6,409,863 B1 | 6/2002 | Williams et al. |
| 6,423,012 B1 | 7/2002 | Kato et al. |
| 6,425,877 B1 | 7/2002 | Edwards |
| 6,432,986 B2 | 8/2002 | Levin |
| 6,440,061 B1 | 8/2002 | Wenner et al. |
| 6,443,947 B1 | 9/2002 | Marko et al. |
| 6,445,939 B1 | 9/2002 | Swanson et al. |
| 6,450,975 B1 | 9/2002 | Brennan et al. |
| 6,450,989 B2 | 9/2002 | Dubrul et al. |
| 6,464,650 B2 | 10/2002 | Jafari et al. |
| 6,468,202 B1 | 10/2002 | Irion et al. |
| 6,468,297 B1 | 10/2002 | Williams et al. |
| 6,485,475 B1 | 11/2002 | Chelly |
| 6,491,940 B1 | 12/2002 | Levin |
| 6,494,894 B2 | 12/2002 | Mirarchi |
| 6,500,130 B2 | 12/2002 | Kinsella et al. |
| 6,500,189 B1 | 12/2002 | Lang et al. |
| 6,503,087 B1 | 1/2003 | Eggert et al. |
| 6,503,185 B1 | 1/2003 | Waksman et al. |
| 6,511,418 B2 | 1/2003 | Shahidi et al. |
| 6,514,249 B1 | 2/2003 | Maguire et al. |
| 6,517,478 B2 | 2/2003 | Khadem |
| 6,524,129 B2 | 2/2003 | Cote et al. |
| 6,524,299 B1 | 2/2003 | Tran et al. |
| 6,524,323 B1 | 2/2003 | Nash et al. |
| 6,526,302 B2 | 2/2003 | Hassett |
| 6,527,753 B2 | 3/2003 | Sekine et al. |
| 6,529,756 B1 | 3/2003 | Phan et al. |
| 6,533,754 B1 | 3/2003 | Hisamatsu et al. |
| 6,536,437 B1 | 3/2003 | Dragisic |
| 6,537,294 B1 | 3/2003 | Boyle et al. |
| 6,543,452 B1 | 4/2003 | Lavigne |
| 6,544,230 B1 | 4/2003 | Flaherty et al. |
| 6,549,800 B1 | 4/2003 | Atalar et al. |
| 6,551,239 B2 | 4/2003 | Renner et al. |
| 6,568,388 B2 | 5/2003 | Kent |
| 6,569,146 B1 | 5/2003 | Werner et al. |
| 6,569,147 B1 | 5/2003 | Evans et al. |
| 6,571,131 B1 | 5/2003 | Nguyen |
| 6,572,538 B2 | 6/2003 | Takase |
| 6,572,590 B1 | 6/2003 | Stevens et al. |
| 6,579,285 B2 | 6/2003 | Sinofsky |
| 6,585,639 B1 | 7/2003 | Kotmel et al. |
| 6,585,717 B1 | 7/2003 | Wittenberger et al. |
| 6,585,794 B2 | 7/2003 | Shimoda et al. |
| 6,591,130 B2 | 7/2003 | Shahidi |
| 6,596,009 B1 | 7/2003 | Jelic |
| 6,607,546 B1 | 8/2003 | Murken |
| 6,612,999 B2 | 9/2003 | Brennan et al. |
| 6,613,066 B1 | 9/2003 | Fukaya et al. |
| 6,616,601 B2 | 9/2003 | Hayakawa |
| 6,616,659 B1 | 9/2003 | de la Torre et al. |
| 6,616,678 B2 | 9/2003 | Nishtala et al. |
| 6,616,913 B1 | 9/2003 | Mautone |
| 6,619,085 B1 | 9/2003 | Hsieh |
| 6,634,684 B2 | 10/2003 | Spiessl |
| 6,638,233 B2 | 10/2003 | Corvi et al. |
| 6,638,268 B2 | 10/2003 | Niazi |
| 6,638,291 B1 | 10/2003 | Ferrera et al. |
| 6,645,193 B2 | 11/2003 | Mangosong |
| 6,652,472 B2 | 11/2003 | Jafari et al. |
| 6,652,480 B1 | 11/2003 | Imran et al. |
| 6,656,166 B2 | 12/2003 | Lurie et al. |
| 6,663,589 B1 | 12/2003 | Halevy |
| 6,669,689 B2 | 12/2003 | Lehmann et al. |
| 6,669,711 B1 | 12/2003 | Noda |
| 6,672,773 B1 | 1/2004 | Glenn et al. |
| 6,673,025 B1 | 1/2004 | Richardson et al. |
| 6,679,871 B2 | 1/2004 | Hahnen |
| 6,685,648 B2 | 2/2004 | Flaherty et al. |
| 6,689,096 B1 | 2/2004 | Loubens et al. |
| 6,689,146 B1 | 2/2004 | Himes |
| 6,702,735 B2 | 3/2004 | Kelly |
| 6,712,757 B2 | 3/2004 | Becker et al. |
| 6,714,809 B2 | 3/2004 | Lee et al. |
| 6,716,183 B2 | 4/2004 | Clayman et al. |
| 6,716,216 B1 | 4/2004 | Boucher et al. |
| 6,716,813 B2 | 4/2004 | Lim et al. |
| 6,719,749 B1 | 4/2004 | Schweikert et al. |
| 6,726,701 B2 | 4/2004 | Gilson et al. |
| 6,755,812 B2 | 6/2004 | Peterson et al. |
| 6,776,772 B1 | 8/2004 | de Vrijer et al. |
| 6,780,168 B2 | 8/2004 | Jellie |
| 6,783,522 B2 | 8/2004 | Fischell |
| 6,783,536 B2 | 8/2004 | Vilsmeier et al. |
| 6,786,864 B2 | 9/2004 | Matsuura et al. |
| 6,796,960 B2 | 9/2004 | Cioanta et al. |
| 6,811,544 B2 | 11/2004 | Schaer |
| 6,817,364 B2 | 11/2004 | Garibaldi et al. |
| 6,817,976 B2 | 11/2004 | Rovengo |
| 6,827,683 B2 | 12/2004 | Otawara |
| 6,827,701 B2 | 12/2004 | MacMahon et al. |
| 6,832,715 B2 | 12/2004 | Eungard et al. |
| D501,677 S | 2/2005 | Becker |
| 6,851,290 B1 | 2/2005 | Meier et al. |
| 6,860,264 B2 | 3/2005 | Christopher |
| 6,860,849 B2 | 3/2005 | Matsushita et al. |
| 6,878,106 B1 | 4/2005 | Herrmann |
| 6,890,329 B2 | 5/2005 | Carroll et al. |
| 6,899,672 B2 | 5/2005 | Chin et al. |
| 6,902,556 B2 | 6/2005 | Grimes et al. |
| 6,913,763 B2 | 7/2005 | Lerner |
| 6,927,478 B2 | 8/2005 | Paek |
| 6,939,361 B1 | 9/2005 | Kleshinski |
| 6,939,374 B2 | 9/2005 | Banik et al. |
| 6,955,657 B1 | 10/2005 | Webler |
| 6,966,906 B2 | 11/2005 | Brown |
| 6,971,998 B2 | 12/2005 | Rosenman et al. |
| 6,979,290 B2 | 12/2005 | Mourlas et al. |

(56) References Cited

U.S. PATENT DOCUMENTS

| | | |
|---|---|---|
| 6,984,203 B2 | 1/2006 | Tartaglia et al. |
| 6,991,597 B2 | 1/2006 | Gellman et al. |
| 6,997,931 B2 | 2/2006 | Sauer et al. |
| 6,997,941 B2 | 2/2006 | Sharkey et al. |
| 7,004,173 B2 | 2/2006 | Sparks et al. |
| 7,008,412 B2 | 3/2006 | Maginot |
| 7,011,654 B2 | 3/2006 | Dubrul et al. |
| 7,022,105 B1 | 4/2006 | Edwards |
| 7,043,961 B2 | 5/2006 | Pandey |
| 7,052,474 B2 | 5/2006 | Castell et al. |
| 7,056,284 B2 | 6/2006 | Martone et al. |
| 7,056,303 B2 | 6/2006 | Dennis et al. |
| 7,074,197 B2 | 7/2006 | Reynolds et al. |
| 7,074,426 B2 | 7/2006 | Kochinke |
| 7,097,612 B2 | 8/2006 | Bertolero et al. |
| 7,108,677 B2 | 9/2006 | Courtney et al. |
| 7,108,706 B2 | 9/2006 | Hogle |
| 7,128,718 B2 | 10/2006 | Hojeibane et al. |
| 7,131,969 B1 | 11/2006 | Hovda et al. |
| 7,140,480 B2 | 11/2006 | Drussel et al. |
| D534,216 S | 12/2006 | Makower et al. |
| 7,160,255 B2 | 1/2007 | Saadat |
| 7,169,140 B1 | 1/2007 | Kume |
| 7,169,163 B2 | 1/2007 | Becker |
| 7,172,562 B2 | 2/2007 | McKinley |
| 7,174,774 B2 | 2/2007 | Pawar et al. |
| 7,182,735 B2 | 2/2007 | Shireman et al. |
| 7,184,827 B1 | 2/2007 | Edwards |
| 7,214,201 B2 | 5/2007 | Burmeister et al. |
| 7,233,820 B2 | 6/2007 | Gilboa |
| 7,235,099 B1 | 6/2007 | Duncavage et al. |
| 7,237,313 B2 | 7/2007 | Skujins et al. |
| 7,252,677 B2 | 8/2007 | Burwell et al. |
| 7,282,057 B2 | 10/2007 | Surti et al. |
| 7,294,345 B2 | 11/2007 | Haapakumpu et al. |
| 7,294,365 B2 | 11/2007 | Hayakawa et al. |
| 7,313,430 B2 | 12/2007 | Urquhart et al. |
| 7,316,168 B2 | 1/2008 | van der Knokke et al. |
| 7,316,656 B2 | 1/2008 | Shireman et al. |
| 7,318,831 B2 | 1/2008 | Alvarez et al. |
| 7,322,934 B2 | 1/2008 | Miyake et al. |
| 7,326,235 B2 | 2/2008 | Edwards |
| 7,338,467 B2 | 3/2008 | Lutter |
| 7,343,920 B2 | 3/2008 | Toby et al. |
| 7,359,755 B2 | 4/2008 | Jones et al. |
| 7,361,168 B2 | 4/2008 | Makower et al. |
| 7,366,562 B2 | 4/2008 | Dukesherer |
| 7,371,210 B2 | 5/2008 | Brock et al. |
| 7,381,205 B2 | 6/2008 | Thommen |
| 7,410,480 B2 | 8/2008 | Muni et al. |
| 7,419,497 B2 | 9/2008 | Muni et al. |
| 7,438,701 B2 | 10/2008 | Theeuwes et al. |
| 7,442,191 B2 | 10/2008 | Hovda et al. |
| 7,452,351 B2 | 11/2008 | Miller et al. |
| 7,454,244 B2 | 11/2008 | Kassab et al. |
| 7,462,175 B2 | 12/2008 | Chang et al. |
| 7,471,994 B2 | 12/2008 | Ford et al. |
| 7,481,218 B2 | 1/2009 | Djupesland |
| D586,465 S | 2/2009 | Faulkner et al. |
| D586,916 S | 2/2009 | Faulkner et al. |
| 7,488,313 B2 | 2/2009 | Segal et al. |
| 7,488,337 B2 | 2/2009 | Saab et al. |
| 7,493,156 B2 | 2/2009 | Manning et al. |
| 7,500,971 B2 | 3/2009 | Chang et al. |
| D590,502 S | 4/2009 | Geisser et al. |
| 7,520,876 B2 | 4/2009 | Ressemann et al. |
| 7,532,920 B1 | 5/2009 | Ainsworth et al. |
| 7,544,192 B2 | 6/2009 | Eaton et al. |
| 7,559,925 B2 | 7/2009 | Goldfarb et al. |
| 7,615,005 B2 | 11/2009 | Stefanchik et al. |
| 7,625,335 B2 | 12/2009 | Deichmann et al. |
| 7,632,291 B2 | 12/2009 | Stephens et al. |
| 7,634,233 B2 | 12/2009 | Deng et al. |
| 7,641,644 B2 | 1/2010 | Chang et al. |
| 7,641,668 B2 | 1/2010 | Perry et al. |
| 7,645,272 B2 | 1/2010 | Chang et al. |
| 7,648,367 B1 | 1/2010 | Makower et al. |
| 7,654,997 B2 | 2/2010 | Makower et al. |
| 7,680,244 B2 | 3/2010 | Gertner et al. |
| 7,686,798 B2 | 3/2010 | Eaton et al. |
| 7,717,933 B2 | 5/2010 | Becker |
| 7,720,521 B2 | 5/2010 | Chang et al. |
| 7,727,186 B2 | 6/2010 | Makower et al. |
| 7,727,226 B2 | 6/2010 | Chang et al. |
| 7,736,301 B1 | 6/2010 | Webler et al. |
| 7,740,642 B2 | 6/2010 | Becker |
| 7,753,929 B2 | 7/2010 | Becker |
| 7,753,930 B2 | 7/2010 | Becker |
| 7,771,409 B2 | 8/2010 | Chang et al. |
| 7,775,968 B2 | 8/2010 | Mathis |
| 7,799,048 B2 | 9/2010 | Hudson et al. |
| 7,803,150 B2 | 9/2010 | Chang et al. |
| 7,833,282 B2 | 11/2010 | Mandpe |
| 7,837,672 B2 | 11/2010 | Intoccia |
| 7,840,254 B2 | 11/2010 | Glossop |
| 7,854,744 B2 | 12/2010 | Becker |
| D630,321 S | 1/2011 | Hamilton, Jr. |
| 7,875,050 B2 | 1/2011 | Samson et al. |
| D632,791 S | 2/2011 | Murner |
| 7,883,717 B2 | 2/2011 | Varner et al. |
| 7,896,891 B2 | 3/2011 | Catanese, III et al. |
| 7,951,132 B2 | 5/2011 | Eaton et al. |
| 7,988,705 B2 | 8/2011 | Galdonik et al. |
| 7,993,353 B2 | 8/2011 | Roßner et al. |
| 8,002,740 B2 | 8/2011 | Willink et al. |
| 8,014,849 B2 | 9/2011 | Peckham |
| 8,016,752 B2 | 9/2011 | Armstrong et al. |
| 8,025,635 B2 | 9/2011 | Eaton et al. |
| 8,080,000 B2 | 12/2011 | Makower et al. |
| 8,088,063 B2 | 1/2012 | Fujikura et al. |
| 8,088,101 B2 | 1/2012 | Chang et al. |
| 8,090,433 B2 | 1/2012 | Makower et al. |
| 8,104,483 B2 | 1/2012 | Taylor |
| 8,114,062 B2 | 2/2012 | Muni et al. |
| 8,114,113 B2 | 2/2012 | Becker |
| 8,123,722 B2 | 2/2012 | Chang et al. |
| 8,142,422 B2 | 3/2012 | Makower et al. |
| 8,147,545 B2 | 4/2012 | Avior |
| 8,167,821 B2 | 5/2012 | Sharrow |
| 8,277,386 B2 | 10/2012 | Ahmed et al. |
| 8,317,816 B2 | 11/2012 | Becker |
| 8,337,454 B2 | 12/2012 | Eaton et al. |
| 8,337,518 B2 | 12/2012 | Nance et al. |
| 8,388,642 B2 | 3/2013 | Muni et al. |
| 8,403,954 B2 | 3/2013 | Santin et al. |
| 8,535,707 B2 | 9/2013 | Arensdorf et al. |
| 8,715,169 B2 | 5/2014 | Chang et al. |
| 8,747,389 B2 | 6/2014 | Goldfarb et al. |
| 8,764,729 B2 | 7/2014 | Muni et al. |
| 8,828,041 B2 | 9/2014 | Chang et al. |
| 8,900,214 B2 | 12/2014 | Nance et al. |
| 8,932,276 B1 | 1/2015 | Morriss et al. |
| 9,220,879 B2 | 12/2015 | Chang et al. |
| 9,241,834 B2 | 1/2016 | Chang et al. |
| 9,399,121 B2 | 7/2016 | Goldfarb et al. |
| 10,524,814 B2 | 1/2020 | Chang et al. |
| 2001/0034530 A1 | 10/2001 | Malackowski et al. |
| 2002/0006961 A1 | 1/2002 | Katz et al. |
| 2002/0010476 A1 | 1/2002 | Mulholland et al. |
| 2002/0055746 A1 | 5/2002 | Burke et al. |
| 2002/0090388 A1 | 7/2002 | Humes et al. |
| 2003/0013985 A1 | 1/2003 | Saadat |
| 2003/0017111 A1 | 1/2003 | Rabito |
| 2003/0040697 A1 | 2/2003 | Pass et al. |
| 2003/0083608 A1 | 5/2003 | Evans et al. |
| 2003/0114732 A1 | 6/2003 | Webler et al. |
| 2003/0158518 A1* | 8/2003 | Schonholz ....... A61B 17/12136 604/104 |
| 2003/0163154 A1 | 8/2003 | Miyata et al. |
| 2004/0015150 A1 | 1/2004 | Zadno-Azizi |
| 2004/0018980 A1 | 1/2004 | Gurney et al. |
| 2004/0034311 A1 | 2/2004 | Mihakcik |
| 2004/0043052 A1 | 3/2004 | Hunter et al. |
| 2004/0058992 A1 | 3/2004 | Marinello et al. |

(56) References Cited

U.S. PATENT DOCUMENTS

| | | |
|---|---|---|
| 2004/0064105 A1 | 4/2004 | Capes et al. |
| 2004/0116958 A1 | 6/2004 | Gopferich et al. |
| 2004/0127820 A1 | 7/2004 | Clayman et al. |
| 2004/0158229 A1 | 8/2004 | Quinn |
| 2004/0181175 A1 | 9/2004 | Clayman et al. |
| 2004/0193073 A1 | 9/2004 | DeMello et al. |
| 2004/0230156 A1 | 11/2004 | Schreck et al. |
| 2004/0236231 A1 | 11/2004 | Knighton et al. |
| 2004/0249243 A1 | 12/2004 | Kleiner |
| 2004/0267347 A1 | 12/2004 | Cervantes |
| 2005/0027249 A1 | 2/2005 | Reifart et al. |
| 2005/0033347 A1* | 2/2005 | Rauker .................. A61F 2/013 606/200 |
| 2005/0055077 A1 | 3/2005 | Marco |
| 2005/0059930 A1 | 3/2005 | Garrison et al. |
| 2005/0089670 A1 | 4/2005 | Large |
| 2005/0107738 A1 | 5/2005 | Slater et al. |
| 2005/0113687 A1 | 5/2005 | Herweck et al. |
| 2005/0113850 A1 | 5/2005 | Tagge |
| 2005/0119590 A1 | 6/2005 | Burmeister et al. |
| 2005/0131316 A1 | 6/2005 | Flagle et al. |
| 2005/0143687 A1 | 6/2005 | Rosenblatt et al. |
| 2005/0149096 A1 | 7/2005 | Hilal et al. |
| 2005/0182319 A1 | 8/2005 | Glossop |
| 2005/0234507 A1 | 10/2005 | Geske et al. |
| 2005/0240147 A1* | 10/2005 | Makower ........... A61B 17/3201 604/96.01 |
| 2005/0244472 A1 | 11/2005 | Hughes et al. |
| 2005/0283221 A1 | 12/2005 | Mann et al. |
| 2006/0004323 A1 | 1/2006 | Chang et al. |
| 2006/0063973 A1 | 3/2006 | Makower et al. |
| 2006/0173382 A1 | 8/2006 | Schreiner |
| 2006/0190022 A1 | 8/2006 | Beyar et al. |
| 2006/0210605 A1* | 9/2006 | Chang .................... A61B 17/24 424/434 |
| 2006/0211752 A1 | 9/2006 | Kohn et al. |
| 2006/0271024 A1 | 11/2006 | Gertner et al. |
| 2007/0020196 A1 | 1/2007 | Pipkin et al. |
| 2007/0112358 A1 | 5/2007 | Abbott |
| 2007/0129751 A1 | 6/2007 | Muni et al. |
| 2007/0135789 A1 | 6/2007 | Chang et al. |
| 2007/0167682 A1 | 7/2007 | Goldfarb et al. |
| 2007/0207186 A1 | 9/2007 | Scanlon et al. |
| 2007/0208252 A1 | 9/2007 | Makower |
| 2007/0208301 A1 | 9/2007 | Evard et al. |
| 2007/0249896 A1 | 10/2007 | Goldfarb et al. |
| 2007/0269385 A1 | 11/2007 | Yun et al. |
| 2007/0282305 A1 | 12/2007 | Goldfarb et al. |
| 2007/0293727 A1 | 12/2007 | Goldfarb et al. |
| 2007/0293946 A1 | 12/2007 | Gonzales et al. |
| 2008/0015544 A1 | 1/2008 | Keith et al. |
| 2008/0033519 A1 | 2/2008 | Burwell et al. |
| 2008/0051804 A1 | 2/2008 | Cottler et al. |
| 2008/0103521 A1 | 5/2008 | Makower et al. |
| 2008/0119693 A1 | 5/2008 | Makower et al. |
| 2008/0188870 A1 | 8/2008 | Andre et al. |
| 2008/0228085 A1 | 9/2008 | Jenkins et al. |
| 2008/0275483 A1 | 11/2008 | Makower et al. |
| 2008/0281156 A1 | 11/2008 | Makower et al. |
| 2008/0287908 A1 | 11/2008 | Muni et al. |
| 2008/0319424 A1 | 12/2008 | Muni et al. |
| 2009/0030274 A1 | 1/2009 | Goldfarb et al. |
| 2009/0088728 A1 | 4/2009 | Dollar et al. |
| 2009/0156980 A1 | 6/2009 | Eaton et al. |
| 2009/0163890 A1 | 6/2009 | Clifford et al. |
| 2009/0187089 A1 | 7/2009 | Say et al. |
| 2009/0187098 A1 | 7/2009 | Makower et al. |
| 2009/0240112 A1 | 9/2009 | Goldfarb et al. |
| 2009/0240237 A1 | 9/2009 | Goldfarb et al. |
| 2010/0087811 A1 | 4/2010 | Herrin et al. |
| 2010/0114066 A1 | 5/2010 | Makower et al. |
| 2010/0198191 A1 | 8/2010 | Clifford et al. |
| 2010/0198247 A1 | 8/2010 | Chang et al. |
| 2010/0198302 A1 | 8/2010 | Shalev |
| 2010/0241155 A1 | 9/2010 | Chang et al. |
| 2011/0166190 A1 | 7/2011 | Anderson et al. |
| 2014/0200444 A1 | 7/2014 | Kim et al. |
| 2014/0296898 A1 | 10/2014 | Chang et al. |
| 2014/0330074 A1 | 11/2014 | Morriss et al. |
| 2014/0336575 A1 | 11/2014 | Muni et al. |
| 2014/0350465 A1 | 11/2014 | Muni et al. |
| 2014/0364725 A1 | 12/2014 | Makower |

FOREIGN PATENT DOCUMENTS

| | | |
|---|---|---|
| CN | 2203154 | 7/1995 |
| CN | 2352818 | 12/1999 |
| DE | 3202878 | 8/1983 |
| DE | 4032096 | 4/1992 |
| DE | 4406077 | 9/1994 |
| DE | 8810044 | 11/1998 |
| DE | 29923582 | 12/2000 |
| DE | 10104663 | 8/2002 |
| DE | 10105592 | 8/2002 |
| EP | 129634 | 1/1985 |
| EP | 257605 | 3/1988 |
| EP | 355996 | 2/1990 |
| EP | 418391 | 3/1991 |
| EP | 427852 | 5/1991 |
| EP | 623582 | 11/1994 |
| EP | 624349 | 11/1994 |
| EP | 744400 | 11/1996 |
| EP | 585757 | 6/1997 |
| EP | 893426 | 1/1999 |
| EP | 1042998 | 10/2000 |
| EP | 1166710 | 1/2002 |
| EP | 1413258 | 4/2004 |
| EP | 1944053 | 7/2008 |
| FR | 2859377 | 3/2005 |
| FR | 2916144 | 11/2008 |
| GB | 2125874 | 3/1984 |
| GB | 2305174 | 4/1997 |
| JP | 53-67935 | 6/1978 |
| JP | 10-24098 | 1/1989 |
| JP | 3-503011 | 7/1991 |
| JP | 3-504935 | 10/1991 |
| JP | 4-221313 | 8/1992 |
| JP | 5-211985 | 8/1993 |
| JP | 6-277296 | 10/1994 |
| JP | 7-327916 | 12/1995 |
| JP | 8-317989 | 12/1996 |
| JP | 11-507251 | 6/1999 |
| JP | 2000-501634 | 2/2000 |
| JP | 2001-501846 | 2/2001 |
| JP | 2001-095815 | 4/2001 |
| JP | 2001-526077 | 12/2001 |
| JP | 2002-028166 | 1/2002 |
| JP | 2002-508214 | 3/2002 |
| JP | 2002-537908 | 11/2002 |
| JP | 2002-538850 | 11/2002 |
| JP | 2003-062080 | 3/2003 |
| JP | 2003-521327 | 7/2003 |
| JP | 2004-357728 | 12/2004 |
| JP | 2005-532869 | 11/2005 |
| JP | 2006-026089 | 2/2006 |
| JP | 2007-537784 | 12/2007 |
| JP | 2009-505691 | 2/2009 |
| RU | 2213530 | 10/2003 |
| SU | 1662571 | 7/1991 |
| WO | WO 90/011053 | 10/1990 |
| WO | WO 90/014865 | 12/1990 |
| WO | WO 91/017787 | 11/1991 |
| WO | WO 92/015286 | 9/1992 |
| WO | WO 92/022350 | 12/1992 |
| WO | WO 94/012095 | 6/1994 |
| WO | WO 96/029071 | 9/1996 |
| WO | WO 97/021461 | 6/1997 |
| WO | WO 99/024106 | 5/1999 |
| WO | WO 99/030655 | 6/1999 |
| WO | WO 99/032041 | 7/1999 |
| WO | WO 00/009192 | 2/2000 |
| WO | WO 00/023009 | 4/2000 |
| WO | WO 00/051672 | 9/2000 |
| WO | WO 00/053252 | 9/2000 |

(56) References Cited

FOREIGN PATENT DOCUMENTS

| WO | WO 01/045572 | 6/2001 |
|---|---|---|
| WO | WO 01/054558 | 8/2001 |
| WO | WO 01/056481 | 8/2001 |
| WO | WO 01/070325 | 9/2001 |
| WO | WO 01/074266 | 10/2001 |
| WO | WO 01/097895 | 12/2001 |
| WO | WO 02/062269 | 8/2002 |
| WO | WO 03/049603 | 6/2003 |
| WO | WO 03/063703 | 8/2003 |
| WO | WO 03/105657 | 12/2003 |
| WO | WO 04/006788 | 1/2004 |
| WO | WO 04/018980 | 3/2004 |
| WO | WO 04/026391 | 4/2004 |
| WO | WO 04/082525 | 9/2004 |
| WO | WO 05/018730 | 3/2005 |
| WO | WO 05/077450 | 8/2005 |
| WO | WO 05/089670 | 9/2005 |
| WO | WO 05/117755 | 12/2005 |
| WO | WO 06/034008 | 3/2006 |
| WO | WO 06/078884 | 7/2006 |
| WO | WO 06/107957 | 10/2006 |
| WO | WO 06/116597 | 11/2006 |
| WO | WO 06/118737 | 11/2006 |
| WO | WO 06/135853 | 12/2006 |
| WO | WO 07/111636 | 10/2007 |
| WO | WO 07/124260 | 11/2007 |
| WO | WO 08/036149 | 3/2008 |
| WO | WO 08/045242 | 4/2008 |
| WO | WO 08/051918 | 5/2008 |
| WO | WO 08/134382 | 11/2008 |

OTHER PUBLICATIONS

Aust, R., et al. 'The Functional Size of the Human Maxillary Ostium in Vivo' Acta. Otolaryn. (9178) vol. 78 pp. 432-435.
Baim, D.S., MD 'Grossman's Cardiac Catheterization, Angiography, and Intervention' (2000) Lippincott Williams & Wilkins pp. 76, 84 & 214.
Barrett, S. 'Be Wary of Neurocranial Restructuring (NCR)' Chirobase; Jul. 2003; www.chirobase.org/06DD/ncr.html.
Bartal, N. 'An Improved stent for Use in the Surgical Management of Congenital Posterior Choanal Atresia' J. Laryngol. Otol (1988) vol. 102 pp. 146-147.
Becker, A.E. 'Restenosis After Angioplasty' The Lancet (1988) vol. 331, No. 8584 p. 532.
Bellis, M. History of the Catheter-Balloon Catheter—Thomas Fogarty. www.inventors.about.com/library/inventors/blcatheter.htm?p=1.
Benninger et al.; Adult Chronic Rhinosinusitis: Definitions, Diagnosis, Epidemiology, and Pathophysiology Arch Otolaryngol Head and Neck Surg. vol. 129 (Sep. 2003) pp. A1-S32.
Bent et al. 'The Frontal Cell as a Cause of Frontal Sinus Obstruction' American Journal of Rhinology, vol. 8, No. 4 (1994) pp. 185-191.
Binner et al. 'Fiber-Optic Transillumination of the Sinuses: A Comparison of the Value of Radiography and Transillumination in Antral Disease' Clinical Otolaryngology. vol. 3 (1978) pp. 1-11.
Brown, C.L. et al., 'Safety and Feasibility of Balloon Catheter Dilation of Paranasal Sinus Ostia: A Preliminary Investigation' Annals of Otology, Rhinology & Laryngology (2006) vol. 115, No. 4 pp. 293-299.
Casiano et al. 'Endoscopic Lothrop Procedure: The University of Miami Experience' American Journal of Rhinology, vol. 12, No. 5 (1998) pp. 335-339.
Casserly, I.P. et al., Chapter 7. 'Guides and Wires in Percutaneous Coronary Intervention' Strategic Approaches in Coronary Intervention (2006) Lippincott Williams & Wilkins pp. 91-99.
Chien, Y.W. et al. 'Nasal Systemic Drug Delivery' Drugs and Pharmaceutical Sciences, vol. 39, pp. 60-63.
Cohen et al. 'Endoscopic Sinus Surgery: Where we are and where we're going' Current Opinion in Otolaryngology & Head and Neck Surgery, vol. 13 (2005) pp. 32-38.
Colla, A. et al., 'Trihaloacetylated Enol Ethers—General Synthetic Procedure and Heterocyclic Ring Closure Reactions with Hydroxylamine' Synthesis, (Jun. 1991) pp. 483-486.
Costa, M.N. et al. 'Endoscopic Study of the Intranasal Ostium in External Dacryocystorhinostomy Postoperative. Influence of Saline Solution and 5-Flurorouracil' Clinics (2007) vol. 62, Issue1, pp. 41-46.
Cussler, E.L. 'Diffusion: Mass transfer in Fluid Systems' Cambridge University Press (1996).
Davis, G.E. et al. 'A Complication from Neurocranial Restructuring' Arch Otolaryngol Head Neck Surg. vol. 129 (Apr. 2003) pp. 472-474.
Deutschmann, R. et al. 'A Contribution to the Topical Treatment of [Maxillary] Sinusitis Preliminary Communication' Stomat DDR 26, (1976) pp. 585-592.
Domb, A. et al. 'Handbook of Biodegradable Polymers' Harwood Academic Publishers (1997).
Doyle Nasal Splints, Jan. 25, 2007; www.doylemedical.com/nasalsplints.htm.
Draf, W. 'Endonasal Micro-Endoscopic Frontal Sinus Surgery: the Fulda Concept' Op Tech Otolaryngol Head Neck Surg. vol. 2 (1991) pp. 234-240.
Edmond, C. et al. 'ENT Surgical Stimulator' Nov. 1989.
ENT Checklist; Physical Examination Performance Checklist [date of publication unknown].
Eremychev, V.A. 'Needles for Puncture and Drainage of the Maxillary Sinus' Meditsinskaya Tekhnika, No. 5 (1974) pp. 54.55.
Feldman, R.L. et al., 'New Steerable, Ultra-Low-Profile, Fixed Wire Angioplasty Catheter: Initial Experience with the Cordis OrionTM Steerable PTCA Balloon Catheter' Cathet. Cardiovasc. Diagn. (1990) vol. 19, No. 2 pp. 142-145.
Ford, C.N. 'A Multipurpose Laryngeal Injector Device' Otolaryngol. Head Neck Surg. (1990) vol. 103, No. 1 pp. 135-137.
Friedman, M., M.D., et al. 'Frontal Sinus Surgery: Endoscopic Technique' Operative Techniques in Otolaryngology—Head and Neck Surgery. vol. 12, No. 2 (Jun. 2001) pp. 60-65.
Friedman, et al. 'Intraoperative and Postoperative Assessment of Frontal Sinus Patency by Transillumination' Laryngoscope. vol. 110 (Apr. 2000) pp. 683-684.
Friedman, et al 'Middle Turbinate Medialization and Preservation in Endoscopic Surgery' Otolaryngology—Head and Neck Surgery. (2000) vol. 123, No. 1, part 1, pp. 76-80.
Fung, M.K.T. 'Template for Frontal Osteoplastic Flap' Laryngoscope. vol. 96 (1986) pp. 578-579.
Gatot, A. et al. 'Early treatment of Orbital Floor Fractures with Catheter Balloon in Children' Int J. Pediatric Otorhinolaryngol (1991) vol. 21 pp. 97-101.
Gerus, I.I. et al. 'β-Ethoxyvinyl Polyfluroroalkyl Ketones—Versatile Synthones in Fluoroorganic Chemistry' Journal of Fluorine Chemistry. vol. 69 (1994) pp. 195-198. Elsevier Science S.A.
Good, R.H. 'An Intranasal Method for Opening the Frontal Sinus Establishing the Largest Possible Drainage' Laryngoscope. vol. 18 (1908) pp. 266-274.
Gopferich 'Polymer Degradation and Erosion: Mechanisms and Application' Eur. J. Parm. Biophar. vol. 42 (1996) pp. 1-11.
Gorlov, D.V. et al 'Acylation of 2-Methoxypropene with Anhydrides and Halides of Perflurocarboxylic Acids in the Presence of Tertiary Amines' Russian Chemical Bulletin. vol. 48 No. 9 (Sep. 1999) pp. 1791-1792. Kluwer Academic/Plenum Publishers.
Gottmann, et al. 'Balloon Dilatation in the Nasal Cavity and Paranasal Sinuses' CIRSE. (Sep. 25, 2004) pp. 1-27.
Gottmann, et al. 'Balloon Dilatation of Recurrent Ostial Occlusion of the Frontal Sinus' CIRSE Abstract (Mar. 2001) B-04353.
Gottman, et al., Balloon Dilatation of Recurrent Ostial Occlusion of the Front Sinus OASIS—Online Abstract Submission and Invitation System, 1996-2006, Coe Truman Technologies, Inc.
Gottmann, et al. 'Successful Treatment of Recurrent Post-Operative Frontal Sinus Stenoses by Balloon Dilatation' CIRSE. (Oct. 5, 2002).
Gottmann, D. 'Treatment of Stenoses of Upper Air Routes by Balloon Dilation' Proceeding of the 83rd Annual Convention of Association of West German ENT Physicians (1999).

(56) References Cited

OTHER PUBLICATIONS

Gupta, D. et al., 'Dacrystitis Secondary to an Iatrogenic Foreign Body in the Lacrimal Apparatus' Ear, Nose & Throat Journal (2009) www.findarticles.com/p/articles/mi_m0BUM/is_7_88/ai_n32428620/.
Hashim, et al. 'Balloon Compression of the Intermaxillary Sinus for Intractable Post Traumatic Bleeding from the Maxillary Artery' Scandinavian Journal of Plastic and reconstruction Surgery and Hand Surgery (1999) vol. 33 pp. 321-324.
Hojo, M. et al, 'Electrophilic Substitutions of Olefinic Hydrogens II. Acylation of Vinyl Ethers and N Vinyl Amides Chemistry Letters' (1976) pp. 499-502. Chemical Society of Japan.
Hopf, J.U.G. et al. 'Minature Endoscopes in Otorhinolaryngologic Applications' Min Invas Ther & Allied Technol. (1998) vol. 7, No. 3 pp. 209-218.
Hosemann, W. et al. A Dissection Course on Endoscopic Endonasal Sinus Surgery (2005) Endo-Press, Tuttlingen pp. 4-37.
Hosemann, W. et al. 'Endonasal Frontal Sinusotomy in Surgical Management of Chronic Sinusitis: A Critical Evaluation' American Journal of Rhinology. vol. 11, No. 1 (1997) pp. 1-9.
Hosemann, M.E. et al. 'Experimentelle Untersuchungen sur Wundheilung in den Nasennebenholhlen. II. Spontaner Wundschluss und medikamentose Effekte im standardisierten Wundmodell.' HNO 39 (1991) pp. 48-54. 'Experimental investigations on wound healing of the paranasal sinuses. II. Spontaneous wound closure and pharmacological effects in a standardized animal model.' HNO 39 (1991) pp. 48-54.
Hosemann, W.G. et al. 'Minimally Invasive Endonasal Sinus Surgery' Thieme, Stuttgart, New York (2000).
Hosemann, M.E. et al. 'Normal Wound Healing of the Paranasal Sinuses—Clinical and Experimental Investigations' Eur Arch Otorhinolarygol. vol. 248, (1991) pp. 390-394.
Hosemann, W. et al. 'Behandlung nach Nasennebenhohleneingriffen, part 2: Theapeutische Maßnahem' HNO akutell 7 (1999) pp. 291-302.
Hospital Corpsman Sick Call Screener's Handbook. Naval Hospital Great Lakes (Apr. 1999) www.brooksidepress.org/Products/Operationa. Medicine/DATA. 2001 pp. 1-6.
Hybels, R.L. 'Transillumination During Osteoplastic Frontal Sinusotomy' The Laryngoscope. vol. 91 (Sep. 1981) pp. 1560.
Ijaduola, T.G.A. 'Use of a Foley Catheter for Short-Term Drainage in Frontal Sinus Surgery' The Journal of Laryngology and Otology. (1989) vol. 103. pp. 375.378.
Ingals, E.F. 'New Operation and Instruments for Draining the Frontal Sinus' Ann. Otol. Rhinol. Layyngol. vol. 14 (1905) pp. 644-649.
Iro, H. et al., 'A New Device for Frontal Sinus Endoscopy: First Clinical Report' Otolaryngol. Head Neck Surg. (2001) vol. 125 No. 6 pp. 613-616.
Jacobs, J.B. '100 Years of Frontal Sinus Surgery' Laryngoscope. vol. 107 (1997) pp. 1-36.
K-Splint Internal Nasal Splints; Jan. 25, 2007; www.invotec.net/rhinology/ksplint.html.
Kaiser, H. et al 'Cortizontherapie, Corticoide in Klinik und Praxis' Thieme, Stuggart (1992) pp. 390-401.
Kennedy, D.W., M.D. et al. 'Diseases of the Sinuses: Diagnosis and Management' (Copyright 2001) by B.C. Decker Inc.
Khomutov, S.M. et al. 'Dissolution of a Mixture of Steroids in Cyclodextrin Solutions: A Model Description' Pharmaceutical Chemistry Journal. vol. 35, No. 11 (Nov. 2001) pp. 627-629.
Kingdom, T.T. et al. 'Image-Guided Surgery of the Sinuses: Current Technology and Applications' Otolaryngol. Clin. North Am. vol. 37, No. 2 (Apr. 2004) pp. 381-400.
Klossek, J.M. et al. 'Local Safety of Intranasal Trimcinolone Acentonide: Clinical and Histological Aspects of Nasal Mucosa in the Long-Term Treatment of Perennial Allergic Rhinitis' Rhinology. vol. 39, No. 1 (2001) pp. 17-22.
Kozlov et al. 'Diagnosis and Treatment of Sinusitis by YAMIK Sinus Catheters' Rhinology (1996) vol. 34, pp. 123-124.
Kuhn, et al. 'The Agger Nasi Cell in Frontal Recess Obstruction: An Anatomic, Radiology and Clinical Correlation' Operative Techniques in Otolaryngology—Head and Neck Surgery. vol. 2, No. 4 (1991) pp. 226-231.
Laliberte, F. et al. 'Clinical and Pathologic Methods to Assess the Long-Term Safety of Nasal Corticosteroids' Allergy. vol. 55, No. 8 (2000) pp. 718-722.
Lang, E.V., et al., 'Access Systems for Puncture at an Acute Angle' J. Vasc. Interv. Radiol. (1995) vol. 6, No. 5 pp. 711-713.
Lanza, D.C. 'Postoperative Care and Avoiding Frontal Recess Stenosis' International Advanced Sinus Symposium Jul. 21-24, 1993.
Large, G.C. 'Crystalline Tetracycline Hydrochloride in the Treatment of Acute and Chronic Maxillary Sinusitis' Canada. M.A.J. (1958) vol. 79 pp. 15-16.
Lund, V.J. 'Maximal Medical Therapy for Chronic Rhinosinusitis' Otolaryngol Clin N. Am. vol. 38 (2005) pp. 1301-1310.
Maran, A.G.D. et al. 'The Use of the Foley Balloon Catheter in the Tripod Fracture' J. Laryngol. Otol. (1971) vol. 85, Issue 9, pp. 897-902.
May, M. et al. 'Frontal Sinus Surgery: Endonasal Drainage Instead of an External Osteopolstic Approach' Op Tech Otolaryngo Head Neck Surgery. 6 (1995) pp. 184-192.
Medtronic, xomed.com—MicroFrance Catalog Browser. Www.xomcat.com/xomfrance/index.php?zone=both&cat=18&sub=58&prodline=1272 (Dec. 31, 2003) pp. 1-2.
Mehan, V.K. et al., 'Coronary Angioplasty through 4 French Diagnostic Catheters' Cathet. Cardiovasc. Diagn. (1993) vol. 30, No. 1 pp. 22-26.
Mellor, J.M. et al 'Synthesis of Trifluromethylnaphthalenes' Tetrahedron. vol. 56 (2000) pp. 10067-10074. Elsevier Science Ltd.
Metson, R., et al., 'Endoscopic Treatment of Sphenoid Sinusitis' Otolaryngology. Head Neck Surg. (1996) vol. 114, No. 6 pp. 736-744.
Metson, R. 'Holmium: YAG Laser Endoscopic Sinus Surgery: A Randomized Controlled Study' Laryngoscope. vol. 106, Issue 1, Supplement 77 (Jan. 1996) pp. 1-18.
Miller, et al. 'Management of Fractures of the Supraorbital Rim' Journal of Trauma. vol. 18, No. 7 (Jul. 1978) pp. 507-512.
Min, Y-G et al. 'Mucociliary Activity and Histopathology of Sinus Mucosa in Experimental Maxillary Sinusitis: A Comparison of Systemic Administration of Antibiotic and Antibiotic Delivery by Polylactic Acid Polymer' Laryngoscope. vol. 105 (Aug. 1995) pp. 835-842.
Mols, B. 'Movable Tool Tip for Keyhole Surgery' Delft Outlook, vol. 3 (2005) pp. 13-17.
Mooney, M.R., et al., 'Monorail™ Piccolino Catheter: A New Rapid Exchange/Ultralow Profile Coronary Angioplasty System' Cathet. Cardiovasc. Diagn. (1990) vol. 20, No. 2 pp. 114-119.
Moriguchi, T. et al. 'Additional-Elimination Reaction in the Trifluoroacetylation of Electron-Rich Olefins' J. Org. Chem. vol. 60, No. 11 (1995) pp. 3523.3528. American Chemical Society.
Park, K. et al. 'Biodegradable Hydrogels for Durg Delivery' (1993) Technomic Publishing Inc. Lancaster.
Piccirillo, J.F. et al. 'Physchometric and Clinimetric Validity of the 20-Item Sino-Nasal Outcome test (SNOT-20)' Copyright 1996 Washington University, St. Louis, MO.
Piers, et al. 'A Flexible Distal Tip with Two Degrees of Freedom for Enhanced Dexterity in Endoscopic Robot Surgery' Proceedings 13th Micromechanics Europe Workshop (2002) pp. 271-274.
Podoshin, L et al. 'Balloon Technique for Treatment of Frontal Sinus Fractures' The journal of Laryngology & Otology (1967), vol. 81. pp. 1157-1161.
Pownell, P.H. et al., 'Diagnostic Nasal Endoscopy' plastic & Reconstructive Surgery (1997) vol. 99, Iss5 pp. 1451-1458.
Prince, et al. 'Analysis of the Intranasal Distribution of Ointment' J Otolaryngol. vol. 26 (1997) pp. 357-360.
Ramsdale, D.R., Illustrated Coronary Intervention: A case-oriented approach, (2001) Martin Dunitz Ltd. pp. 1-5.
Ritter, F.N. et al., Atlas of Paranasal Sinus Surgery (1991) Igaku-Shoin Medical Pub. pp. 1-81.
Robison, J. Mathews, M.D. 'Pressure Treatment of Maxillary Sinusitis' J.A.M.A. (May 31, 1952) pp. 436-440.

(56) References Cited

OTHER PUBLICATIONS

Robison, J. Mathews, M.D. 'Pressure Treatment of Purulent Maxillary Sinusitis' Texas State Journal of Medicine (May 1952) pp. 281-288.
St. Croix et al. 'Genes Expressed in Human Tumor Endothelium' Science, vol. 289 (May 15, 2000) pp. 1197-1202.
Sama, A., et al., 'Current Opinions on the Surgical Management of Frontal Sinus Disease' ENT News. www.pinpointmedical.com/ent-news (2009) vol. 17, No. 6 pp. 60-63.
Sanborn, T.A. et al., 'Percutaneous Endocardial Transfer and Expression of Genes to the Myocardium Utilizing Fluoroscopic Guidance' Catheter Cardiovasc. Interv. (2001) vol. 52, No. 2 pp. 260-266.
Sawbones Catalog 2001, Pacific Research Laboratories, Inc., Vashon Washington 98070 USA.
Saxon, R.R. et al., 'Technical Aspects of Accessing the Portal Vein During the TIPS Procedure' J. Vasc. Interv. Radiol. (1997) vol. 8, No. 5 pp. 733-744.
Schaefer, S.D., M.D. 'Rhinology and Sinus Disease: A Problem-Oriented Approach' (Copyright 1988) by Mosby, Inc.
Schneider. Pfizer Ad for Softip [date of publication unknown].
Shah, N.J. et al., 'Endoscopic Pituitary Surgery—A Beginner's Guide' Indian Journal of Otolaryngology and Head and Neck Surgery (2004) vol. 56, No. 1 pp. 71-78.
Shah, N.J. 'Functional Endoscopic Sinus Surgery' (1999); found at bhj.org/journal/1999_4104_oct99/sp_659.htm.
Single-Pole and Multi-Pole Lightguides for UV Spot Light Curing Systems.
Sinusitis, Maxillary, Acute Surgical Treatment. Http://www.emedicine.com/ent/topic340.htm. Aug. 29, 2006. pp. 1-11.
Sobol, et al. 'Sinusitis, Maxillary, Acute Surgical Treatment.' eMedicine. Retrieved from the Internet: <<http://emedicine.medscape.com/article/862030-print>> (Nov. 16, 2010) pp. 1-11.
Stammberger, H. 'Komplikationen entzundlicher Nasennebenhohlenerkrankungen eischließ iatrogen bedingter Komplikationen' Eur Arch Oti-Rhino-Laryngol Supple. (Jan. 1993) pp. 61-102.
Stammberger, et al. Chapter 3 'Special Endoscopic Anatomy of the Lateral Nasal Wall and Ethmoidal Sinuses' Functional Endoscopic Sinus Surgery. (1991) Ch. 3, pp. 49-87.
Strohm, et al. Die Behandlung von Stenosen der oberen Luftwege mittels rontgenologisch gesteuerter Ballondilation (Sep. 25, 1999) pp. 1-4.
Strohm, et al 'Le Traitement Des Stenoses Voies Aeriennes Superieures Par Dilation Ay Balloon' Sep. 25, 1999.
Strohm, et al. 'Treatment of Stenoses of the Upper Airways by Balloon Dilation' Sudwestdeutscher Abstract 45 (Sep. 25, 1999) pp. 1-3.
SurgTrainer Product Information 'Incisive Human Nasal Model for ESS Training' Surg Trainer, Ltd. Ibaraki, Japan (2004) www1.accsnet.ne.jp/~juliy/st/en/partslist.html.
Tabor, M.H. et al., 'Symptomatic Bilateral Duct Cysts in a Newborn—Rhinoscopic Clinic' Ear, Nose & Throat Journal (2003) www.findarticles.com/p/articles/mi_m0BUM/is_2_82/ai_98248244 pp. 1-3.
Tarasov, D.I. et al. 'Application of Drugs Based on Polymers in the Treatment of Acute and Chronic Maxillary Sinusitis' Vestn Otorinoloaringol. vol. 6 (1978) pp. 45-47.
http://www.technologyforlife.com.au/ent/nasal.html; Nasal Surgery and Accessories; Jan. 25, 2007.
Terumo. Medi-Tech. Boston Scientific. (1993) Ad of Guidewire.
The Operating Theatre Journal (www.otjonline.com) 'Disposable Medical Device for Wound Disclosure/The Tristel Purple Promotion—A Collaboration between Tristel PLC and Karl Storz Ednoscopy (UK) Ltd.' p. 4.
Weber, R. et al. 'Endonasale Stirnhohlenchirugie mit Langzeiteinlage eines Platzhalters' Laryngol. Rhinol. Otol. vol. 76 (1997) pp. 728-734. (English Abstract).
Weber, R. et al., 'Videoendoscopic Analysis of Nasal Steroid Distribution' Rhinology. vol. 37 (1999) pp. 69-73.
Weiner, R.I., D.O., et al., 'Development and Application of Transseptal Left Heart Catheterization' Cathet. Cardiovasc. Diagn. (1988) vol. 15, No. 2, pp. 112-120.
Wiatrak, B.J., et al., 'Unilateral Choanal Atresia: Initial Presentation and Endoscopic Repair' International Journal of Pediatric Otorhinolaryngology (1998) vol. 46, pp. 27-35.
Woog, et al. 'Paranasal Sinus Endoscopy and Orbital Fracture Repair' Arch Ophthalmol. vol. 116 (May 1998) pp. 688-691.
Wormald, P.J., et al., 'The 'Swing-Door' Technique for Uncinectomy in Endoscopic Sinus Surgery' The Journal of Laryngology and Otology (1998) vol. 112, pp. 547-551.
Xomed-Treace. Bristol-Myers Squibb. Ad for Laser Shield II. Setting the Standards for Tomorrow. [date of publication unknown].
Yamauchi, Y. et al., 'Development of a Silicone Model for Endoscopic Sinus Surgery' Proc International Journal of Computer Assisted Radiology and Surgery vol. 99 (1999) p. 1039.
Yamauchi, Y., et al., 'A Training System for Endoscopic Sinus Surgery with Skill Evaluation' Computer Assisted Radiology and Surgery (2001) with accompanying poster presentation.
Yanagisawa et al. 'Anterior and Posterior Fontanelles.' Ear, Nose & Throat Journal (2001) vol. 80. pp. 10-12.
Zimarino, M., M.D., et al., 'Initial Experience with the EuropassTM: A new Ultra-Low Profile Monorail Balloon Catheter' Cathet. Cardiovasc. Diagn. (1994) vol. 33, No. 1, pp. 76-79.
Australian Office Action, Examiners First Report dated Apr. 8, 2010 for Application No. AU 2005274794.
Australian Office Action dated Nov. 12, 2014 for Application No. 2010226594, 4 pages.
Australian Office Action dated Oct. 22, 2015 for Application No. 2010226594, 5 pages.
Canadian Office Action dated Apr. 4, 2016 for Application No. 2,755,321, 6 pages.
Chinese Office Action dated Feb. 5, 2013 for Application No. 201080013878.9, 11 pages.
Chinese Office Action dated Oct. 30, 2013 for Application No. 201080013878.9, 9 pages.
Chinese Office Action dated Jan. 14, 2014 for Application No. 201080013878.9, 7 pages.
European Communication dated Jun. 19, 2009 for Application No. EP 05773189.
European Communication dated Sep. 4, 2008 for Application No. EP 05773189.
European Exam Report dated Feb. 8, 2007 for Application No. EP 02716734.5.
European Exam Report dated Feb. 22, 2006 for Application No. EP 02716734.5.
European Search Report and Written Opinion dated Sep. 11, 2009 for Application No. EP 06815174.
European Search Report dated Sep. 27, 2011 for Application No. EP 10182961.
European Office Action dated Feb. 27, 2015 for Application No. 10710518.1, 3 pages.
International Preliminary Report on Patentability dated Aug. 7, 2006 for Application No. PCT/US2005/25371.
International Preliminary Report on Patentability and Written Opinion dated Sep. 25, 2007 for Application No. PCT/US2006/02004.
International Preliminary Report on Patentability and Written Opinion dated Apr. 7, 2009 for Application No. PCT/US2007/021170.
International Preliminary Report on Patentability and Written Opinion dated May 5, 2009 for Application No. PCT/US2006/036960.
International Preliminary Report on Patentability dated Feb. 15, 2008 for Application No. PCT/US2005/013617.
International Preliminary Report on Patentability and Written Opinion dated Nov. 18, 2008 for Application No. PCT/US2007/011449.
International Preliminary Report on Patentability and Written Opinion dated Oct. 13, 2009 for Application No. PCT/US2008/059786.
International Preliminary Report on Patentability and Written Opinion dated Oct. 27, 2009 for Application No. PCT/US2008/061343.
International Search Report and Written Opinion dated Apr. 10, 2006 for Application No. PCT/US2005/25371.
International Search Report and Written Opinion dated Jul. 21, 2008 for Application No. PCT/US2005/033090.

(56) References Cited

OTHER PUBLICATIONS

International Search Report and Written Opinion dated Sep. 12, 2008 for Application No. PCT/US2007/16214.
International Search Report and Written Opinion dated Sep. 17, 2008 for Application No. PCT/US2008/059786.
International Search Report and Written Opinion dated Sep. 17, 2008 for Application No. PCT/US2008/061343.
International Search Report and Written Opinion dated Oct. 1, 2008 for Application No. PCT/US2007/011449.
International Search Report and Written Opinion dated Oct. 6, 2010 for Application No. PCT/US2010/040548.
International Preliminary Report on Patentability and Written Opinion dated Sep. 20, 2011 for Application No. PCT/US2010/027837, 9 pages.
International Search Report dated Jun. 3, 2002 for Application No. PCT/EP2002/01228.
International Search Report dated May 8, 2007 for Application No. PCT/US2006/016026.
International Search Report dated Aug. 29, 2007 for Application No. PCT/US2006/002004.
International Search Report dated Sep. 25, 2007 for Application No. PCT/US2006/037167.
International Search Report dated Oct. 19, 2007 for Application No. PCT/US2007/003394.
International Search Report dated May 29, 2008 for Application No. PCT/US2007/021170.
International Search Report dated May 29, 2008 for Application No. PCT/US2007/021922.
International Search Report dated Jul. 1, 2008 for Application No. PCT/US2006/022745.
International Search Report dated Jul. 3, 2008 for Application No. PCT/US2006/029695.
International Search Report dated Jul. 7, 2008 for Application No. PCT/US2007/016213.
International Search Report dated Jul. 8, 2008 for Application No. PCT/US2007/011474.
International Search Report dated Jul. 17, 2008 for Application No. PCT/US2006/036960.
International Search Report dated Aug. 25, 2008 for Application No. PCT/US2008/000911.
International Search Report dated Sep. 10, 2008 for Application No. PCT/US2007/016212.
International Search Report dated Oct. 15, 2008 for Application No. PCT/US2008/061048.
International Search Report dated Nov. 30, 2009 for Application No. PCT/US2009/057203.
International Search Report dated Dec. 10, 2009 for Application No. PCT/US2009/052236.
International Search Report dated Dec. 16, 2009 for Application No. PCT/US2009/050800.
International Search Report dated Mar. 31, 2010 for Application No. PCT/US2009/069143.
International Search Report dated Jul. 8, 2010 for Application No. PCT/US2010/027837.
International Search Report dated Mar. 25, 2011 for Application No. PCT/US2010/062161.
International Search Report dated Mar. 28, 2011 for Application No. PCT/US2010/061850.
International Search Report dated Mar. 31, 2011 for Application No. PCT/US2010/060898.
International Search Report dated Aug. 9, 2011 for Application No. PCT/US2011/038751.
Japanese Office Action dated Jan. 23, 2014 for Application No. 2012-500966, 2 pages.
Japanese Office Action dated Sep. 30, 2014 for Application No. 2012-500966, 3 pages.
Mexican Office Action dated Mar. 20, 2014 for Application No. MX/a/2011/009837, 4 pages.
Mexican Office Action dated Jul. 2, 2015 for Application No. MX/a/2011/009837, 3 pages.
Partial European Search Report dated Sep. 20, 2007 for Application No. EP 07252018.
Partial European Search Report dated Mar. 25, 2008 for Application No. EP 07252018.
Partial International Search Report dated Feb. 7, 2012 for Application No. PCT/US2011/052321.
Russian Office Action dated Apr. 14, 2014 for Application No. 2011142301, 19 pages.
Supplemental European Search Report dated Jan. 29, 2010 for Application No. EP 07836108.
Supplemental European Search Report dated Feb. 2, 2010 for Application No. EP 07836109.
Supplemental European Search Report dated Feb. 17, 2010 for Application No. EP 07836110.
Supplemental European Search Report dated Mar. 1, 2010 for Application No. EP 05778834.
Supplemental European Search Report dated Mar. 16, 2010 for Application No. EP 06718986.
Supplemental European Search Report dated Jun. 22, 2010 for Application No. EP 06784759.
Supplemental European Search Report dated Sep. 23, 2010 for Application No. EP 08746715.
Supplemental European Search Report dated Jan. 28, 2011 for Application No. EP 07777004.
Supplemental European Search Report dated Mar. 31, 2011 for Application No. EP 05798331.
Supplemental European Search Report dated Aug. 30, 2011 for Application No. EP 06800540.
Supplemental European Search Report dated Sep. 29, 2011 for Application No. EP 07750248.
Supplemental Partial European Search Report dated Jun. 2, 2008 for Application No. EP 05773189.
Supplemental Partial European Search Report dated Jul. 1, 2009 for Application No. EP 06815285.
Supplemental Partial European Search Report dated Nov. 19, 2010 for Application No. EP 06751637.
USPTO Office Action dated Sep. 16, 2005 for U.S. Appl. No. 10/259,300.
USPTO Office Action dated Jul. 7, 2006 for U.S. Appl. No. 10/259,300.
USPTO Office Action dated Feb. 13, 2007 for U.S. Appl. No. 10/259,300.
USPTO Office Action dated Oct. 9, 2007 for U.S. Appl. No. 10/259,300.
USPTO Office Action dated Jan. 24, 2008 for U.S. Appl. No. 10/259,300.
USPTO Office Action dated Oct. 6, 2008 for U.S. Appl. No. 10/259,300.
USPTO Office Action dated May 29, 2007 for U.S. Appl. No. 10/912,578.
USPTO Office Action dated Nov. 14, 2007 for U.S. Appl. No. 10/912,578.
USPTO Office Action dated Dec. 10, 2007 for U.S. Appl. No. 10/912,578.
USPTO Office Action dated Oct. 18, 2007 for U.S. Appl. No. 11/037,548.
USPTO Office Action dated Dec. 6, 2007 for U.S. Appl. No. 11/037,548.
USPTO Office Action dated Apr. 9, 2008 for U.S. Appl. No. 11/037,548.
USPTO Office Action dated Nov. 28, 2007 for U.S. Appl. No. 11/234,395.
USPTO Office Action dated Sep. 12, 2008 for U.S. Appl. No. 10/829,917.
USPTO Office Action dated Nov. 17, 2008 for U.S. Appl. No. 10/829,917.
USPTO Office Action dated Mar. 18, 2009 for U.S. Appl. No. 10/829,917.
USPTO Office Action dated Nov. 9, 2009 for U.S. Appl. No. 10/829,917.
USPTO Office Action dated Oct. 29, 2008 for U.S. Appl. No. 11/347,147.

(56) References Cited

OTHER PUBLICATIONS

USPTO Office Action dated Feb. 4, 2009 for U.S. Appl. No. 11/347,147.
USPTO Office Action dated Aug. 6, 2009 for U.S. Appl. No. 11/347,147.
USPTO Office Action dated Nov. 7, 2008 for U.S. Appl. No. 10/944,270.
USPTO Office Action dated Jan. 28, 2009 for U.S. Appl. No. 10/944,270.
USPTO Office Action dated Apr. 21, 2009 for U.S. Appl. No. 10/944,270.
USPTO Office Action dated Nov. 17, 2008 for U.S. Appl. No. 12/117,582.
USPTO Office Action dated Mar. 3, 2009 for U.S. Appl. No. 12/117,582.
USPTO Office Action dated Aug. 6, 2009 for U.S. Appl. No. 12/117,582.
USPTO Office Action dated Mar. 4, 2009 for U.S. Appl. No. 12/118,931.
USPTO Office Action dated Jul. 30, 2009 for U.S. Appl. No. 12/118,931.
USPTO Office Action dated Nov. 25, 2008 for U.S. Appl. No. 12/117,961.
USPTO Office Action dated Aug. 6, 2009 for U.S. Appl. No. 12/117,961.
USPTO Office Action dated Dec. 5, 2008 for U.S. Appl. No. 12/120,902.
USPTO Office Action dated Oct. 21, 2009 for U.S. Appl. No. 12/120,902.
USPTO Office Action dated Mar. 17, 2009 for U.S. Appl. No. 11/690,127.
USPTO Office Action dated Mar. 23, 2009 for U.S. Appl. No. 11/804,309.
USPTO Office Action dated Mar. 23, 2009 for U.S. Appl. No. 11/926,326.
USPTO Office Action dated Aug. 28, 2009 for U.S. Appl. No. 11/150,847.
U.S. Appl. No. 11/789,705, filed Apr. 24, 2007.
U.S. Appl. No. 11/804,308, filed May 16, 2007.
U.S. Appl. No. 60/844,874, filed Sep. 15, 2006.
U.S. Appl. No. 60/922,730, filed Apr. 9, 2007.
U.S. Appl. No. 61/052,413, filed May 12, 2008.
U.S. Appl. No. 61/084,949, filed Jul. 30, 2008.

* cited by examiner

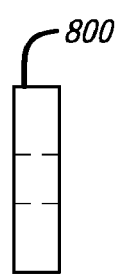
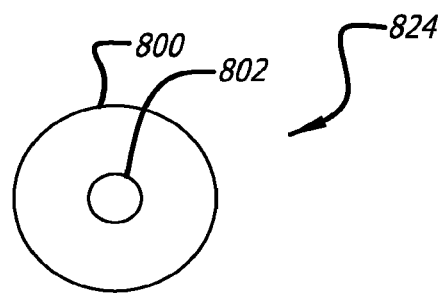
FIG. 24A-1    FIG. 24A-2
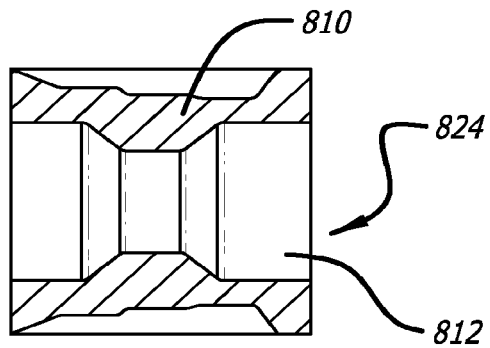
FIG. 24B
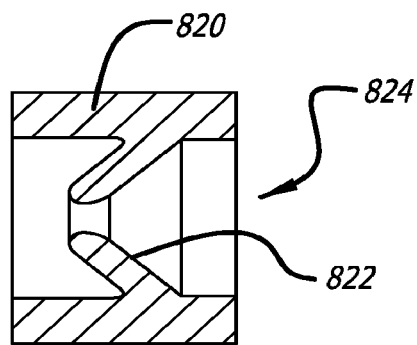
FIG. 24C

GUIDE SYSTEM WITH SUCTION

This application is a continuation of U.S. patent application Ser. No. 15/165,209, entitled "Guide System with Suction," filed May 26, 2016, published as U.S. Pub. No. 2016/0324535 on Nov. 10, 2016, which is a divisional application of U.S. patent application Ser. No. 12/408,524, entitled "Guide System with Suction," filed Mar. 20, 2009, now abandoned.

FIELD OF THE INVENTION

The present invention relates generally to medical devices and methods and more particularly to devices, systems and methods for treating sinusitis.

BACKGROUND

Chronic sinusitis is a medical condition that affects the lives of millions of people every year. In fact, it has been estimated that chronic sinusitis results in 18 million to 22 million physician office visits per year in the United States. Chronic sinusitis refers to inflammation of the paranasal sinuses that lasts for three months or more or that occurs frequently. The condition can be very debilitating, often causing headaches, facial pain, excessive nasal drainage, difficulty breathing through the nose and other symptoms, and often making certain activities such as flying in an airplane very painful. The overall costs to society of chronic sinusitis are enormous, in terms of medical costs, missed days of work, etc.

The paranasal sinuses are air spaces behind the bones of the upper face, between the eyes and behind the forehead, nose and cheeks. On each side of the face there is one set of frontal sinuses (in the forehead), maxillary sinuses (in the cheek bones), ethmoid sinuses (between the eyes) and sphenoid sinuses (farther back behind the eyes). The frontal, maxillary and sphenoid sinuses are all connected to, and drain into, the nasal cavity via openings called ostia ("ostium" singular). The nasal cavity and paranasal sinuses are made of bone covered with mucous tissue, and the mucous tissue has small, hair-like projections called cilia, which move together to sweep mucus through and out of the sinuses as a kind of filter. When the mucosal tissue of the sinuses becomes inflamed, often due to infection, it sometimes swells and can block one or more ostia, thus preventing the movement of mucus from the sinuses to the nasal cavity and thus causing blockage, pressure build-up, and the symptoms of sinusitis. This blockage can sometimes last for long periods of time or recur again and again, causing a great deal of discomfort.

One of the ways to treat sinusitis is by restoring the flow of mucus through and out of the sinuses via the openings (ostia) into the nasal cavity. Typically, the initial therapy attempted in treating sinusitis is drug therapy and nasal sprays—anti-inflammatory agents to reduce inflammation of the mucosal tissue and antibiotics to treat infection. A large number of patients do not respond to nasal spray/drug therapy, however. Patients with chronic or recurring sinusitis may and do not respond to drug therapy may then decide to undergo a surgical procedure.

One form of surgical procedure for treating chronic sinusitis is a called Functional Endoscopic Sinus Surgery ("FESS"). In FESS, a rigid endoscope is inserted into the nose, and a surgeon uses one or more rigid instruments, such as shavers and graspers, to remove diseased or hypertrophic mucosal tissue and bone and in some cases enlarge the ostia of the sinuses to attempt to "open up" and restore normal drainage of the sinuses. These FESS procedures are successful in many cases but do have a number of significant drawbacks. For example, general anesthesia is required for a FESS procedure. Also, because significant amounts of soft tissue and bone are typically removed, FESS can cause significant bleeding and post-operative pain, and thus recovery from surgery can be painful and take many days or even weeks. Because FESS procedures are often associated with significant postoperative bleeding, nasal packing is frequently placed in the patient's nose for some period of time following the surgery. Such nasal packing can be uncomfortable and can interfere with normal breathing, eating, drinking etc. This packing often must be removed and replaced, which can be very uncomfortable. Scar tissue may also have to be removed in the physician's office, in a procedure called a "debridement," which can also be very painful. Also, some patients remain symptomatic even after multiple FESS surgeries. Additionally, some FESS procedures are associated with risks of iatrogenic orbital, intracranial and sinonasal injury. Many otolaryngologists consider FESS an option only for patients who suffer from severe sinus disease (e.g., those showing significant abnormalities under CT scan). Thus, patients with less severe disease may not be considered candidates for FESS and may be left with no option but drug therapy. One of the reasons why FESS procedures can be bloody and painful relates to the fact that instruments having straight, rigid shafts are used. In order to target deep areas of the anatomy with such straight rigid instrumentation, the physician needs to resect and remove or otherwise manipulate any anatomical structures that may lie in the direct path of the instruments, regardless of whether those anatomical structures are part of the pathology.

As an alternative to traditional FESS procedures, the assignee of the present application has invented a number of less invasive/less traumatic systems, devices and methods for treating chronic sinusitis by expanding openings between the nasal cavity and the paranasal sinuses using an expandable dilation device. In some instances, these and other methods for treating sinusitis or other conditions may involve advancing one or more devices into the nasal cavity and/or a paranasal sinus via a guide device, such as a guide catheter. Because the anatomy of the nasal cavity, the paranasal sinuses and the openings between the two is very complex, small and tortuous, and because damage to mucosal tissue in the nasal cavity and sinuses may cause post-operative pain and bleeding, a need exists for guide devices that are relatively easy to use in this anatomy and are as atraumatic as possible. The present disclosure addresses these and other needs.

SUMMARY

Briefly and in general terms, the present disclosure is directed to a system and method for treating paranasal sinuses. In one particular aspect, the disclosed system and method is employed to treat sinusitis.

In one particular embodiment, the system for treating sinuses includes a guide catheter including a catheter shaft configured to receive a balloon catheter and to provide suction while the balloon catheter resides in the catheter shaft. The guide catheter can further include a proximal portion having a first stiffness and a distal portion having a second stiffness less than the first stiffness. The distal portion can be curved and have a diameter which is less than a diameter of the proximal portion. The system can additionally include a valve for sealing the balloon catheter as well as a suction port and vent.

In further embodiments, the system is contemplated to include a guidewire over which the balloon catheter can be advanced. It is also contemplated that the guidewire can be illuminating. Moreover, the distal tip of the guide catheter can be beveled in a manner to facilitate placement behind an ucinate process and can further embody a flexible material providing a less traumatic interface for engaging anatomy such as an ethmoid bulla. The flexibility of the distal tip can be chosen such that it expands to receive a balloon catheter. Additionally, the guide catheter can embody a tapered profile such that a distal portion thereof defines a smaller dimension than a proximal section.

The guide catheter can also include a proximally oriented flange providing a connection to other devices. The flange can be equipped with structure to register with such other devices as well as operator gripping surfaces. A vent is further contemplated to provide suction control.

Various different shapes of the distal end of the guide catheter are also contemplated. In particular, the distal tip can include various shaped flange structures intended to reduce trauma. The tip can also include structure providing visualization under fluoroscopy.

In related methods, treatment of the sinuses can include inserting a guide catheter within a head of a patient and advancing a flexible device through the guide catheter. A suction force is generated about the flexible device and the flexible device is advanced beyond a distal end of the guide catheter and into the patient's sinuses. In one particular aspect, the flexible device is a balloon catheter and the balloon catheter is employed to dilate an ostium of a paranasal sinus. The method can further involve employing a guidewire over which the interventional devices are placed.

Further aspects, details and embodiments of the present disclosure are set forth in the following detailed description of the invention and the accompanying drawings.

BRIEF DESCRIPTION OF THE DRAWINGS

FIGS. 24A-1 through 24C depict various configurations for a sealing structure for a guide catheter.

DETAILED DESCRIPTION

The following detailed description, the accompanying drawings and the above-set-forth Brief Description of the Drawings are intended to describe some, but not necessarily all, examples or embodiments of the invention. The contents of this detailed description do not limit the scope of the invention set forth in the claims.

A number of the drawings in this patent application show anatomical structures of the ear, nose and throat. In general, these anatomical structures are labeled with the following reference letters:

| Nasal Cavity | NC |
| Nasopharynx | NP |
| Frontal Sinus | FS |
| Sphenoid Sinus | SS |
| Sphenoid Sinus Ostium | SSO |
| Maxillary Sinus | MS |

Figure 1:
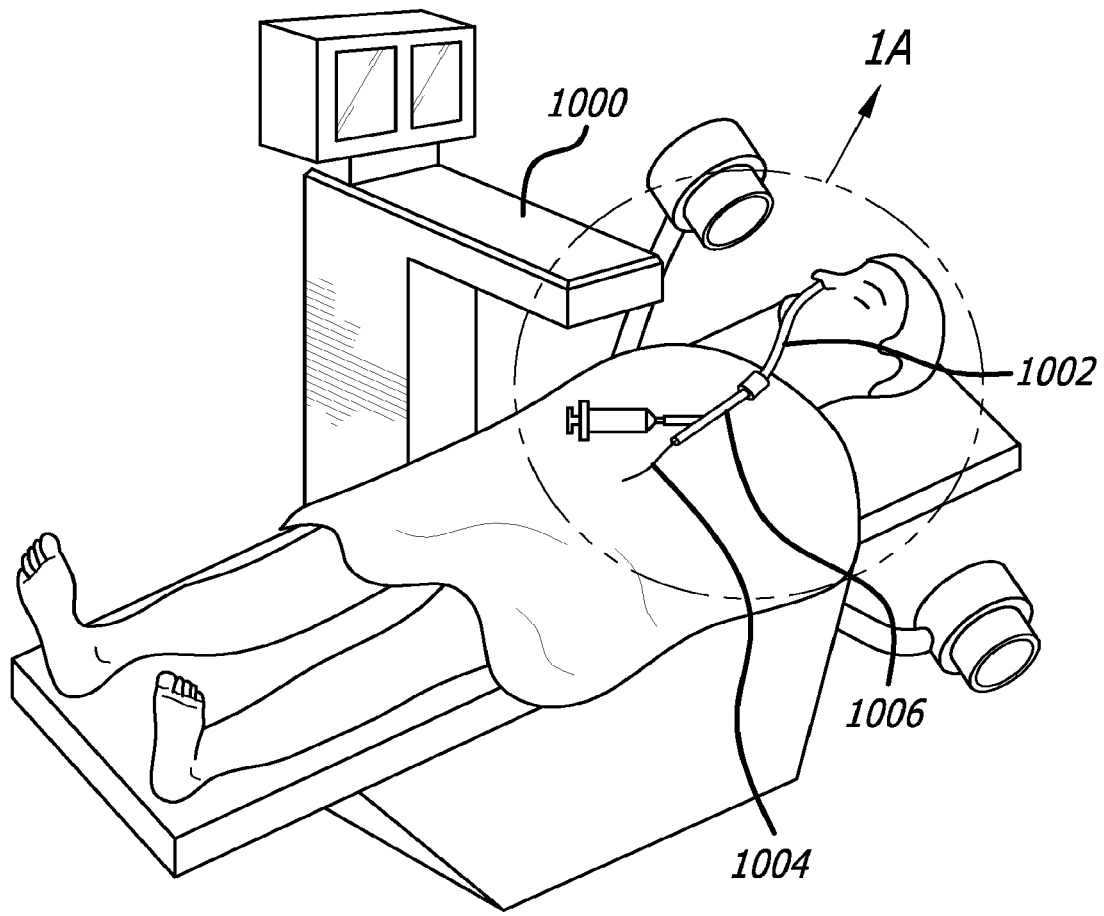
FIG. 1 shows a schematic diagram of a system for catheter-based minimally invasive sinus surgery of the present invention being used to perform a sinus surgery procedure on a human patient.
Figure 1A:
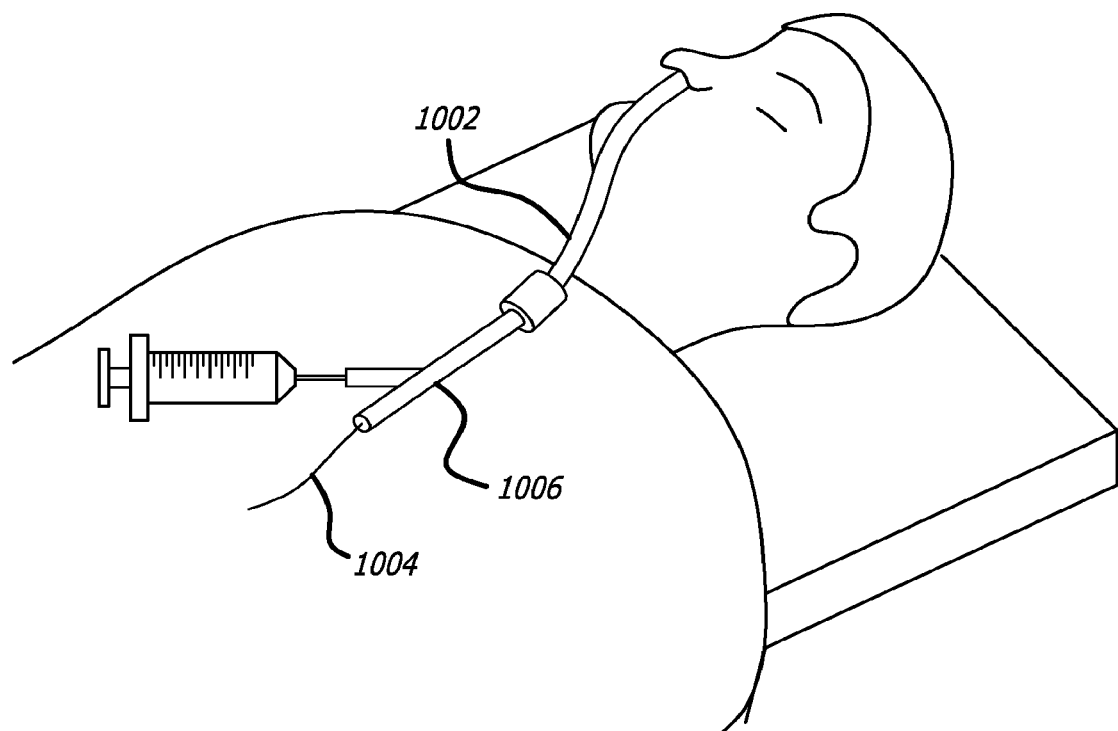
FIG. 1A is an enlarged view of portion "1A" of FIG. 1.

FIGS. 1 and 1A illustrate a patient on an operating table with a minimally invasive surgery system in position to perform a dilation procedure on one or more paranasal sinuses. The system shown includes a C-arm fluoroscope 1000, a first introducing device 1002 (e.g., a guide catheter or guide tube), a second introducing device 1004 (e.g., a guidewire or elongate probe) and a working device 1006 (e.g., a balloon catheter, other dilation catheter, debrider, cutter, etc.).

In some embodiments, the devices 1002, 1004, 1006 may be radiopaque and/or may incorporate radiopaque markers such that C-arm fluoroscope 1000 may be used to image and monitor the positioning of the devices 1002, 1004, 1006 during the procedure. In addition to, or as an alternative to, the use of radiographic imaging, the devices 1002, 1004, 1006 may incorporate and/or may be used in conjunction with one or more endoscopic devices, such as the typical rigid or flexible endoscopes or stereo endocscopes used by otolaryngologists during FESS procedures. Also, in addition to or as an alternative to radiographic imaging and/or endoscopic visualizations, some embodiments of the devices 1002, 1004, 1006 may incorporate sensors which enable the devices 1002, 1004, 1006 to be used in conjunction with image guided surgery systems or other electro-anatomical mapping/guidance systems including but not limited to: VectorVision (BrainLAB AG); HipNav (CASurgica); CBYON Suite (CBYON); InstaTrak, FluoroTrak, ENTrak (GE Medical); StealthStation Treon, iOn (Medtronic); Medivision; Navitrack (Orthosoft); OTS (Radionics); VISLAN (Siemens); Stryker Navigation System (Stryker Leibinger); Voyager, Z-Box (Z-Kat Inc.) and NOGA and CARTO systems (Johnson & Johnson). Commercially available interventional navigation systems can also be used in conjunction with the devices and methods. Further non-fluoroscopic interventional imaging technologies including but not limited to: OrthoPilot (B. Braun Aesculap); PoleStar (Odin Medical Technologies; marketed by Medtronic); SonoDoppler, SonoWand (MISON); CT Guide, US Guide (UltraGuide) etc. may also be used in conjunction with the devices and methods. Guidance under magnetic resonance is also feasible if the catheter is modified to interact with the system appropriately.

The devices and methods of the present invention relate to the accessing and dilation or modification of sinus ostia or other passageways within the ear nose and throat. These devices and methods may be used alone or may be used in conjunction with other surgical or non-surgical treatments, including but not limited to the delivery or implantation of devices and drugs or other substances as described in copending U.S. Patent Application Ser. No. 10/912,578 entitled Implantable Devices and Methods for Delivering Drugs and Other Substances to Treat Sinusitis and Other Disorders filed on Aug. 4, 2004, issued as U.S. Pat. No. 7,361,168 on Apr. 22, 2008, the entire disclosure of which is expressly incorporated herein by reference.

FIGS. 2A-2D are partial sagittal sectional views through a human head showing various steps of a method of gaining access to and treating a paranasal sinus using a guide catheter. Although FIGS. 2A-2D demonstrate a method for accessing and treating a sphenoid paranasal sinus, in alternative embodiments this or analogous methods and devices may be used to access and treat any of the other paranasal sinuses (maxillary, frontal and/or ethmoid).

Figure 2A:
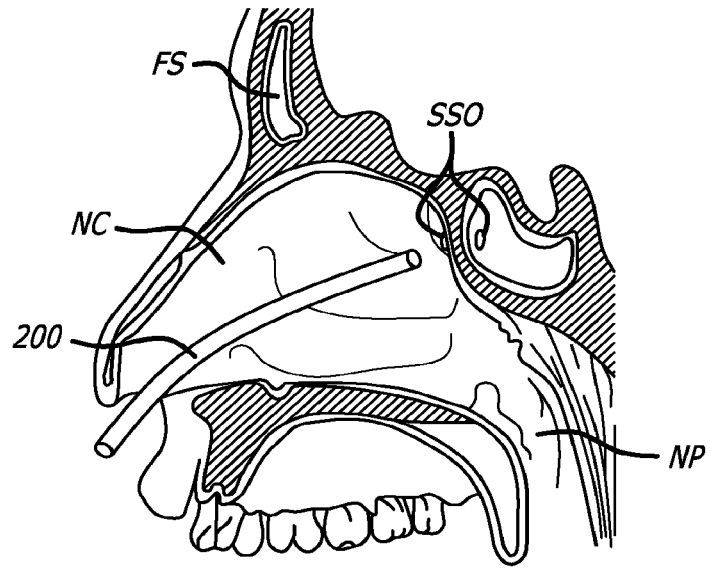
FIGS. 2A through 2D are partial sagittal sectional views through a human head showing various steps of a method for gaining access to a paranasal sinus using a guide and thereafter dilating or remodeling the ostial opening into a sphenoid paranasal sinus.

In FIG. 2A, a first introducing device in the form of a guide catheter 200 is introduced through a nostril and through a nasal cavity NC to a location close to an ostium SSO of a sphenoid sinus SS. The guide catheter 200 may be flexible. Flexible devices are defined as devices with a flexural stiffness less than about 200 pound-force per inch over a device length of one inch. The guide catheter 200 may be straight or it may incorporate one or more preformed curves or bends. In embodiments where the guide catheter 200 is curved or bent, the deflection angle of the curve or bend may be in the range of up to 135°. Examples of specific deflection angles formed by the curved or bent regions of the guide catheter 200 are 0°, 30°, 45°, 60°, 70°, 90°, 120° and 135°. Guide catheter 200 can be constructed from suitable elements like PEBAX, Polyimide, Braided Polyimide, Polyurethane, Nylon, PVC, Hytrel, HDPE, PEEK, metals like stainless steel and fluoropolymers like PTFE, PFA, FEP and EPTFE. Guide catheter 200 can have a variety of surface coatings e.g. hydrophilic lubricious coatings, hydrophobic lubricious coatings, abrasion resisting coatings, puncture resisting coatings, electrically or thermal conductive coatings, radiopaque coatings, echogenic coatings, thrombogenicity reducing coatings and coatings that release drugs.

Figure 2B:
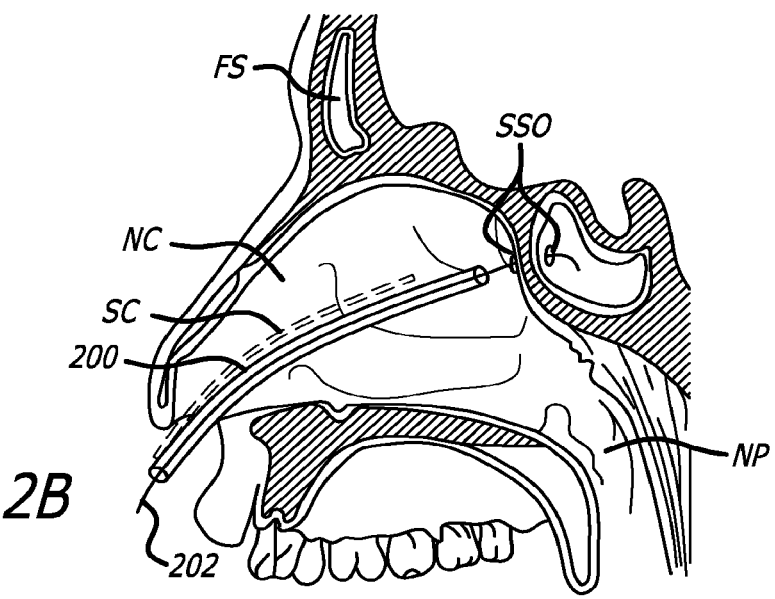

In FIG. 2B, a second introduction device comprising a guidewire 202 is introduced through the first introduction device (i.e., the guide catheter 200) so that the guidewire 202 enters the sphenoid sinus SS through the ostium SSO. Guidewire 202 may be constructed and coated as is common in the art of cardiology.

Figure 2C:
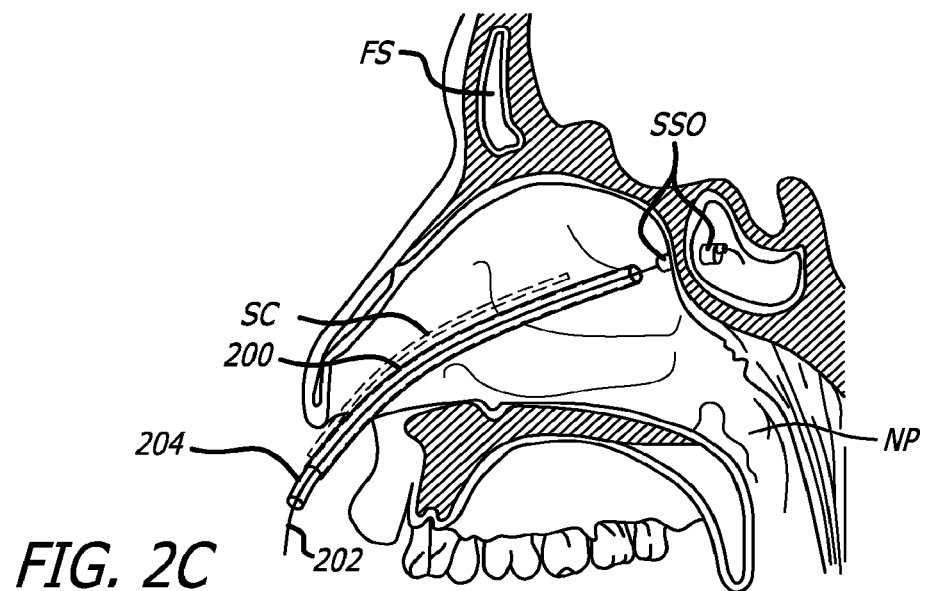
Figure 2D:
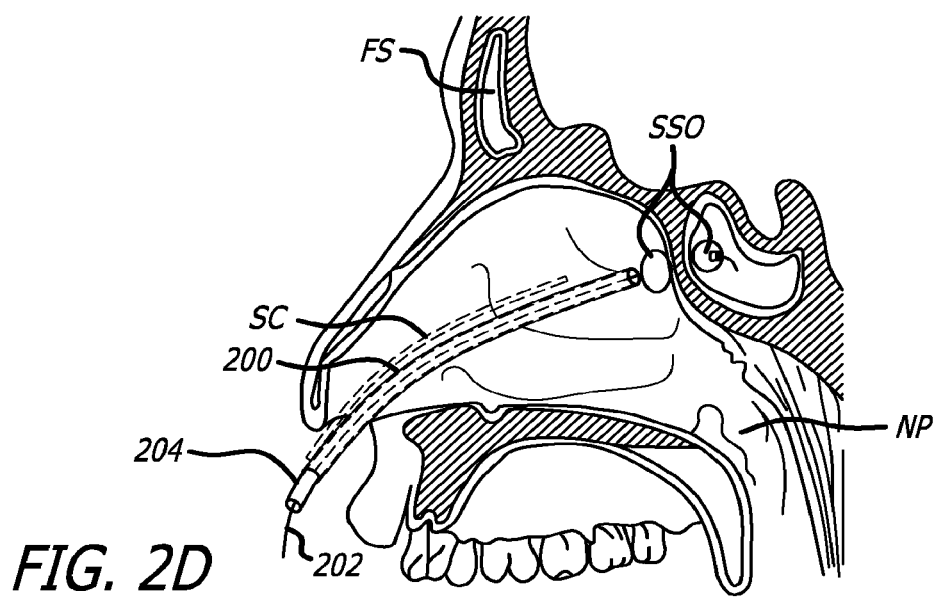

In FIG. 2C, a working device 204, for example a balloon catheter, is introduced over guidewire 202 into the sphenoid sinus SS. Thereafter, in FIG. 2D, the working device 204 is used to perform a diagnostic or therapeutic procedure. In this particular example, the procedure is dilation of the sphenoid sinus ostium SSO, as is evident from FIG. 2D. However, the present invention may also be used to dilate or modify any other sinus ostium or other man-made or naturally occurring anatomical opening or passageway within the nose, paranasal sinuses, nasopharynx or adjacent areas, including but not limited to natural paranasal sinus ostia of the maxillary, frontal and/or ethmoid sinuses. After the completion of the procedure, guide catheter 200, guidewire 202 and working device 204 are withdrawn and removed. In this or any of the procedures described in this patent application, the operator may additionally advance other types of catheters or of the present invention, a guidewire 202 may be steerable (e.g. torquable, actively deformable) or shapeable or malleable. Guidewire 202 may comprise an embedded endoscope or other navigation or imaging modalities including but not limited to fluoroscopic, X-ray radiographic, ultrasonic, radiofrequency localization, electromagnetic, magnetic, robotic and other radiative energy based modalities. In this regard, some of the figures show optional scopes SC is dotted lines. Such optional scopes SC may comprise any suitable types of rigid or flexible endoscopes and such optional scopes SC may be separate from or incorporated into the working devices and/or introduction devices of the present invention.

Optionally, the methods disclosed herein may also comprise the step of cleaning or lavaging anatomy within the nose, paranasal sinus, nasopharynx or nearby structures including but not limited to irrigating and suctioning. The step of cleaning the target anatomy can be performed before or after a diagnostic or therapeutic procedure.

The methods of the present invention may also include one or more preparatory steps for preparing the nose, paranasal sinus, nasopharynx or nearby structures for the procedure, such as spraying or lavaging with a vasoconstricting agent (e.g., 0.025-0.5% phenylephyrine or Oxymetazoline hydrochloride (Neosynephrine or Afrin) to cause shrinkage of the nasal tissues, an antibacterial agent (e.g., provodine iodine (Betadine), etc. to cleanse the tissues, etc.

Figure 3A:
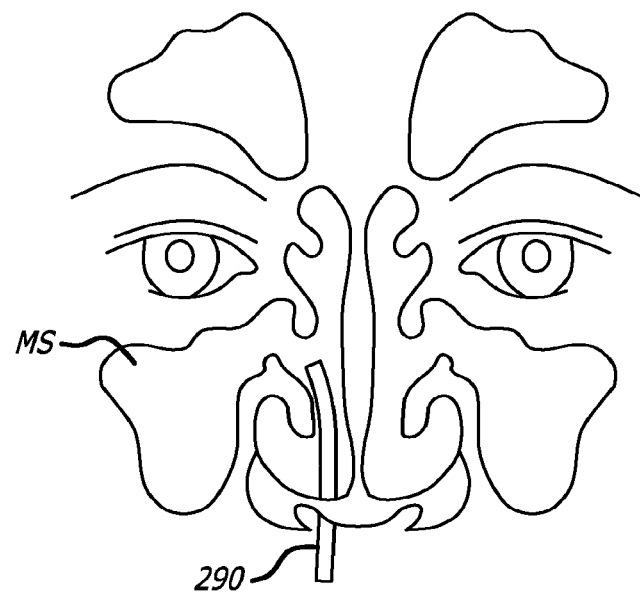
FIGS. 3A through 3D are coronal sectional views through a human head showing various steps of a method for gaining access to a paranasal sinus using a guide and thereafter dilating or remodeling the ostial opening into a maxillary paranasal sinus.
Figure 3B:
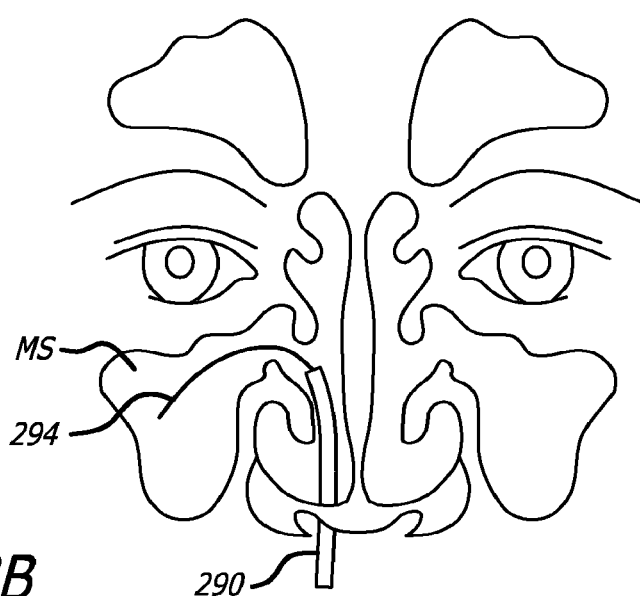
Figure 3C:
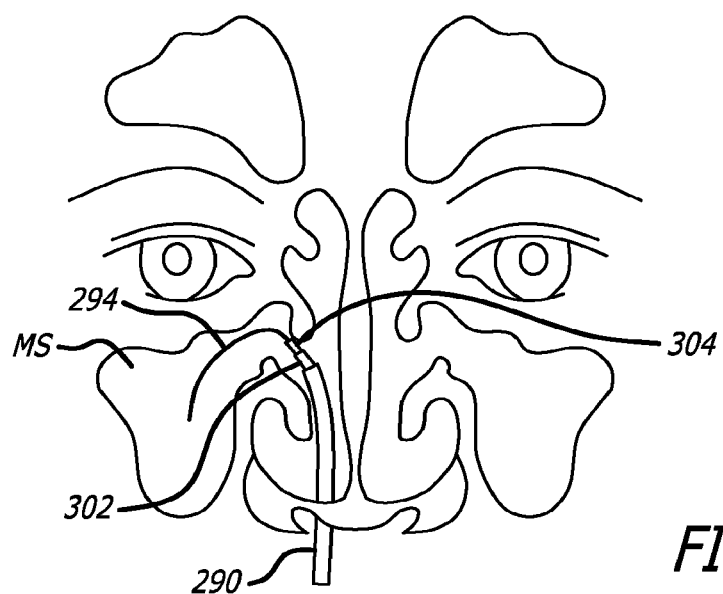
Figure 3D:
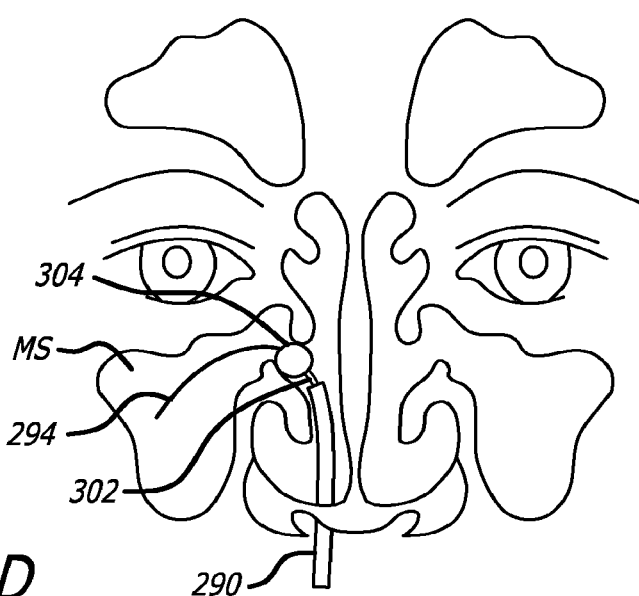

As shown in FIGS. 3A-3D, in one embodiment a maxillary sinus may be treated by dilating an ostium thereto. As shown in FIG. 3A, a guide catheter 290 may be advanced into a patient's nostril to position a distal end thereof adjacent the maxillary sinus ostium. As shown in FIG. 3B, a guidewire 294 may then be advanced through the guide 290 and through the maxillary sinus ostium, into the maxillary sinus. Next, as shown in FIG. 3C, a balloon catheter 302 may be advanced through the guide catheter 290 over the guidewire 294, to position an expandable balloon 304 of the balloon catheter 302 within the maxillary ostium. Then, as shown in FIG. 3D, the expandable balloon 304 may be inflated to dilate the natural paranasal sinus ostium of the maxillary sinus. When the dilation procedure is complete, the guide catheter 290, guidewire 294 and balloon catheter 302 may all be removed from the patient. In an alternative embodiment, the guide catheter 290 and/or the guidewire 294 may be left in the patient, the balloon catheter 302 may be removed, and another flexible device (not shown in the figures) may be advanced over and/or through the guide catheter and/the guidewire 294 into the maxillary sinus to perform an additional procedure. For example, in one embodiment, an irrigation catheter may be advanced through the guide catheter 290 and used to irrigate the sinus. Such an irrigation catheter may be advanced without a guidewire 294 or using a guidewire 294 in alternative embodiments.

FIGS. 4A-4D are partial coronal sectional views through a human head showing various steps of a method of accessing a maxillary paranasal sinus through an artificially created opening into the sinus and dilating the artificial opening, the natural paranasal sinus ostium or both. In some embodiments, rather than accessing a paranasal sinus via the natural sinus ostium, an artificial opening may be made into a sinus. In some embodiments, a guide may be used to then guide a balloon catheter or other dilator (with or without guidewire) through the artificial opening, into the sinus. The dilator may then be advanced to the natural paranasal sinus ostium and used to dilate the natural ostium, may be used to dilate the artificial opening, or both.

Figure 4A:
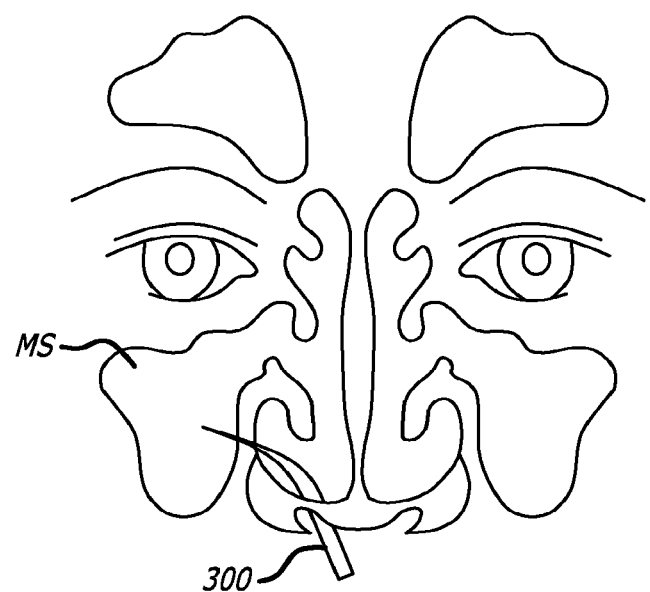
FIGS. 4A through 4D are partial coronal sectional views through a human head showing various steps of a method of accessing a maxillary paranasal sinus through an artificially created opening of the paranasal sinus and then dilating the artificially created opening, the natural paranasal sinus ostium or both.
Figure 4B:
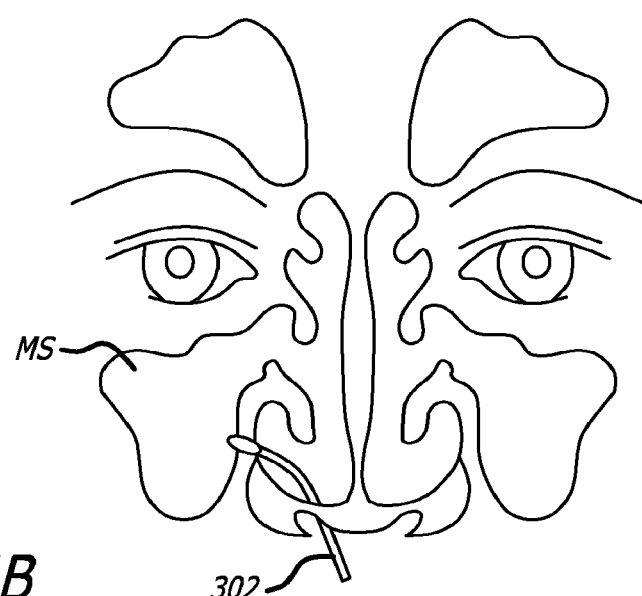
Figure 4C:
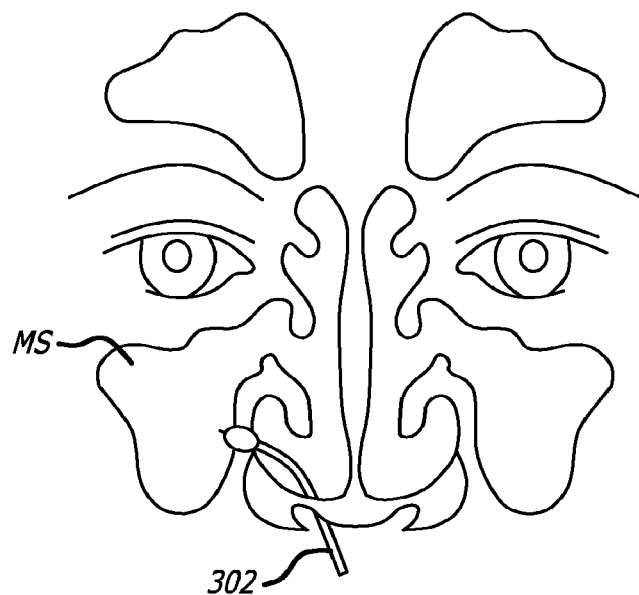
Figure 4D:
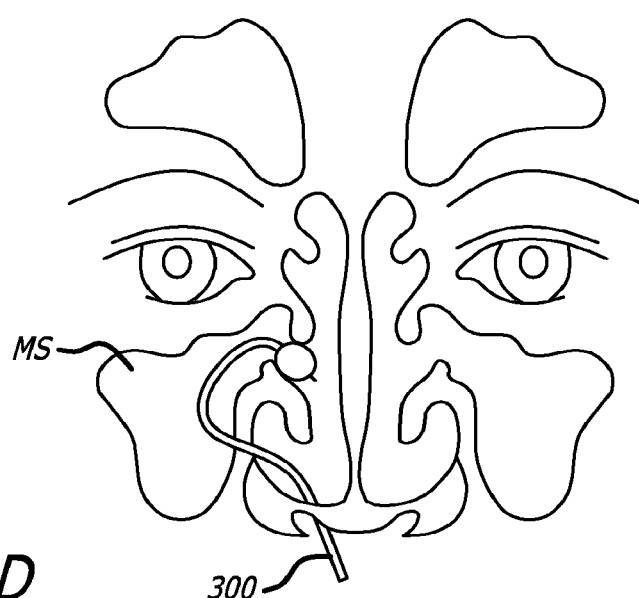

In FIG. 4A, a puncturing device 300 is inserted through a nostril and used to create an artificial opening in a maxillary sinus. Examples of such puncturing devices include but are not limited to straight needles, needles with bent shafts, dissectors, punches, drills, corers, scalpels, burs, scissors, forceps and cutters. In FIG. 4B, puncturing device 300 is withdrawn and a working device, for example a balloon catheter 302, is introduced through the artificial opening into the maxillary sinus. In FIG. 4C, balloon catheter 302 is used to dilate the artificially created opening in the maxillary sinus. After this step, the balloon catheter 302 is withdrawn. In another embodiment, as shown in FIG. 4D, the balloon catheter 302 may be advanced through the artificial opening into the maxillary sinus and then advanced farther into the maxillary sinus to position the balloon of the catheter 302 in the natural paranasal sinus ostium. In some embodiments, this advancement to the natural ostium may be performed after dilating the artificial opening. Alternatively, the balloon catheter 302 may be advanced in some embodiments without dilating the artificial opening.

In some embodiments, a balloon catheter 302 may be advanced over a guidewire to the natural paranasal sinus ostium. Alternatively, the balloon catheter 302 may be advanced without the use of a guidewire in other embodiments. In some embodiments, the puncturing device 300 may have a lumen through which an introduction device (e.g., a guidewire or other elongate probe or member), may be inserted into the maxillary sinus, and the puncturing device 300 may then be removed, leaving such introduction device (e.g., a guidewire or other elongate probe or member) in place. In such cases, the working device (e.g., balloon catheter 302) may incorporate a lumen or other structure that allows the working device (e.g., balloon catheter 300) to be advanced over the previously inserted introduction device (e.g., a guidewire or other elongate probe or member). In some embodiments, the piercing device may include a lumen, and the balloon catheter 302 may be advanced through the piercing device into the maxillary sinus, either with or without a guidewire in various embodiments. Again, similar methods and devices may be used to access and treat other paranasal sinuses in alternative embodiments.

In another alternative embodiment (not shown in FIGS. 4A-4D), a piercing device may be used to create an opening into a maxillary sinus at a different location, and a guide catheter may be used to access the sinus through the opening. For example, in one embodiment the artificial opening may be made through a canine fossa into a maxillary sinus. In another embodiment, a trephine incision may be made into a frontal paranasal sinus. In other embodiments, an artificial opening may be formed into an ethmoid or sphenoid sinus. In some embodiments, a guide may then be placed through the artificial opening and used to access the natural paranasal sinus ostium. In other embodiments, the guide catheter may remain outside the sinus, near the artificial opening, and used to guide a guidewire and/or other device(s) into the sinus. In alternative embodiments, the artificial opening may be dilated, the natural paranasal sinus ostium may be dilated, or both. These methods may be applied to any paranasal sinus. As will be described in greater detail below, any of these guide catheters, whether used to access a paranasal sinus via a natural or artificial opening, may be provided with suction capabilities according to various embodiments of the present invention.

Any of the guide catheters or other luminal devices disclosed herein may have suction capabilities and thus can comprise an arrangement for suctioning an anatomical region through the distal end of the guide catheter or device. In some embodiments, a guide catheter may be provided along with an adapter to attach the guide to a suction source. In another embodiment, a guide catheter may have an integrated or built-in suction attachment, so that an adapter is not necessary. Currently, physicians use a traditional suction device to clear the surgical field when using surgical devices in the nasal cavity and paranasal sinuses. This requires the surgeon to frequently exchange devices, picking up and putting down the traditional suction device many times per case. Allowing the surgeon to suction through the guide catheter while simultaneously passing guidewires, balloons, irrigation catheters and/or the like through the guide catheter can simplify the surgical procedure. A suction adapter can attach to a proximal end of the guide catheter. It can include a valve in-line with an axis of the guide catheter shaft, the valve allowing devices such as guidewires, balloons, and irrigation catheters to be passed through the suction adapter and guide catheter while maintaining suction through the lumen of the guide catheter. Extension tubing can be configured to run offset from the body of the suction adapter. The extension tubing may terminate in a stepped adapter and/or an on-off valve to improve ease of use.

To connect to the guide catheter, a male slip-fit luer can be used. This provides a mechanically secure and airtight seal while allowing for easy rotational adjustment of the guide catheter with respect to the suction adapter. Moreover, a hole through the body of the suction adapter allows for easy control of the amount of suction through the guide catheter. When the hole is not occluded, there is little or no vacuum at the distal end of the guide catheter. The surgeon can partially or fully occlude the hole with his finger to increase the vacuum at the tip of the guide catheter. An on/off switch can be further provided to control suction activation. The switch is placed to "on" and then the hole is occluded to initiate suctioning. Further, a silicone or polyisoprrene valve can be used to maintain a seal around guidewires, balloons or irrigation catheters. The valve is fully closed when no device is present. Extension tubing in the form of lightweight tubing can be used to connect the suction adapter to heavier gauge tubing used commonly in operating rooms. The tubing has sufficient wall thickness to prevent collapse under vacuum but does not add mass or ergonomic challenges to the guide catheter.

Figure 5A:
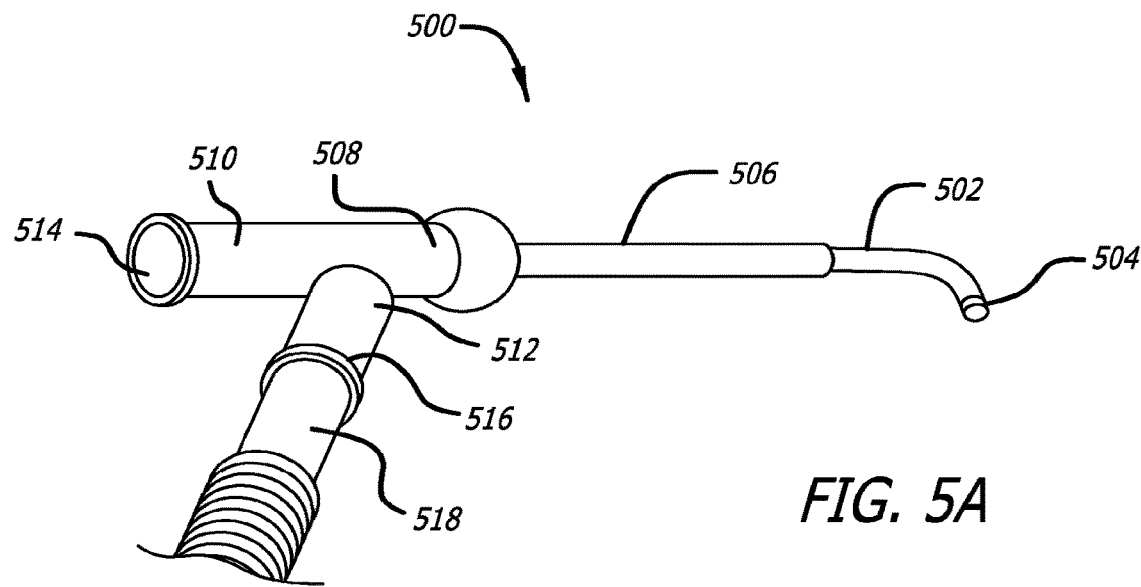
FIG. 5A shows a perspective view of a tubular guide equipped for optional suctioning.

For example, FIG. 5A shows a guide with a proximal adapter for attaching to suction. More specifically, the guide catheter 500 can comprise an elongate tube 502 that may be made of suitable biocompatible materials, including but not limited to metals such as stainless steel, titanium, Nickel-titanium alloy (e.g., Nitinol), etc.; plastics such as PEBAX, PEEK, Nylon, polyethylene, etc. The distal region of elongate tube 502 may comprise a curved, bent or angled region. In some embodiments, the distal end of elongate tube 502 may comprise an atraumatic tip 504. Although various modes of construction may be used, in the example shown, an elongate hypotube 506 is disposed on the outer surface of elongate tube 502 and the proximal end of guide catheter 500 comprises a branched or Y-connector 508. The proximal region of Y-connector 508 comprises a straight arm 510 and a side arm 512. The proximal end of straight arm 510 comprises a suitable hub 514. In one embodiment, hub 514 is a female luer hub. In another embodiment, hub 514 comprises a rotating hemostasis valve such as a Touhy-Borst adapter. The proximal end of side arm 512 comprises a suitable hub 516. In one embodiment, hub 516 comprises a rotating hemostasis valve such as a Touhy-Borst adapter to adjust the amount of suction. Hub 516 is connected to a suction tube 518 that provides suction to guide catheter 500. Thus, guide catheter 500 can be used to provide suction as well as introduce one or more diagnostic, therapeutic or access devices into the anatomy.

Figure 5B:
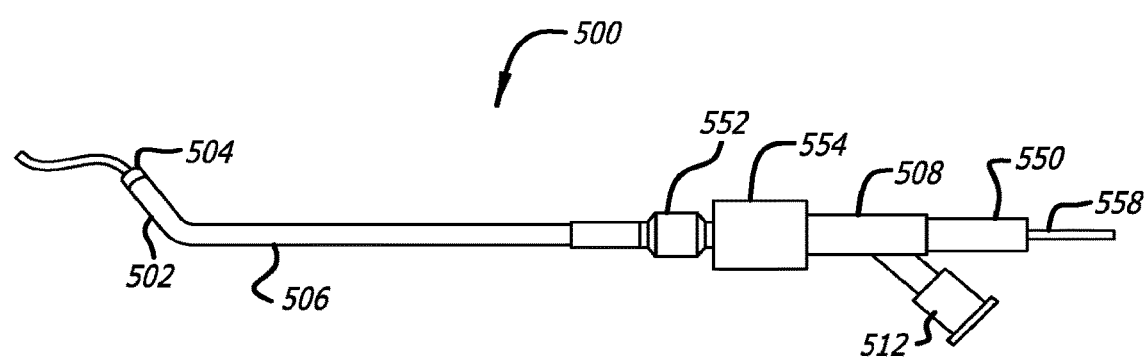
FIG. 5B shows a side view of an alternative embodiment of a tubular guide with a pinch tube.

In an alternative approach, the guide catheter can be further equipped with a pinch tube 550 (See FIG. 5B). The pinch tube is connected to a proximal end of the Y-connecter 508 and can be formed from silicone or another flexible material. Further, a proximal end of the elongate tube 502 can be configured with a female luer 552 which mates with a male luer 554 attached to the Y-connecter 508. In use, the pinch tube 550 is pinched closed by a physician about a guidewire 551 or other device to occlude the lumen extending through the guide to thereby facilitate suctioning. As before, suction forces are applied through the side arm 512.

Figure 6:
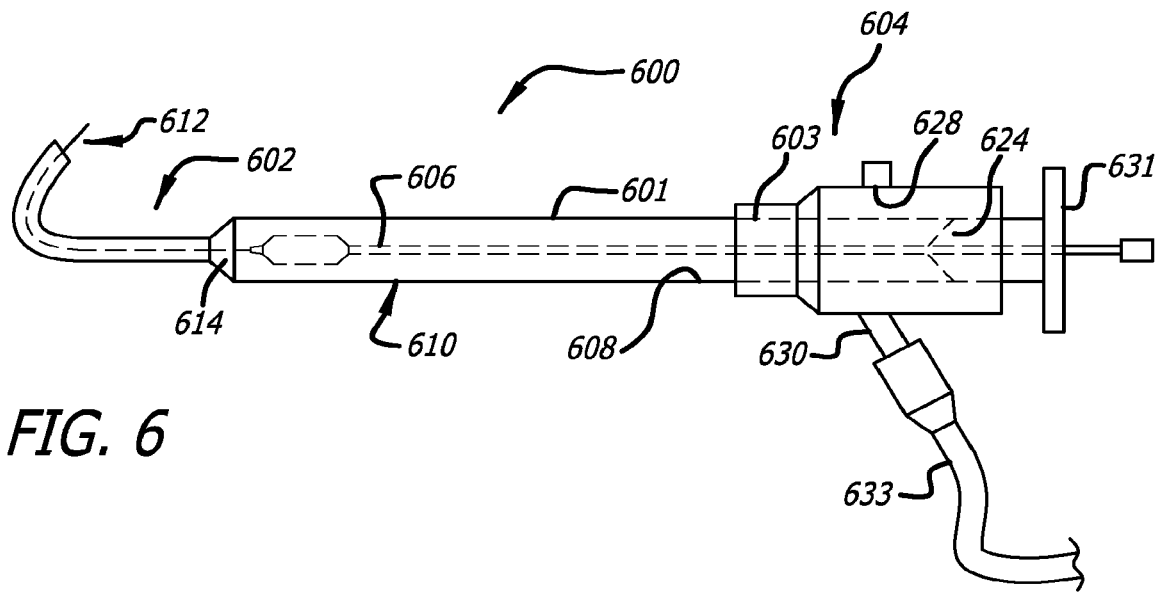
FIG. 6 depicts a partial cross-sectional view of a guide catheter system including a balloon catheter and suction structure.
Figure 7:
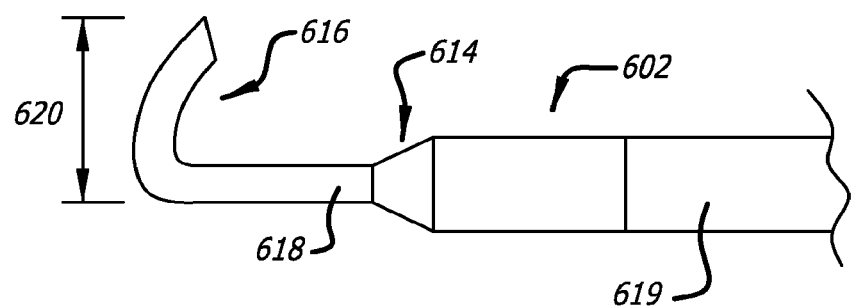
FIG. 7 shows a distal portion of the guide catheter system depicted in FIG. 6.

Turning now to FIGS. 6 and 7, in one embodiment, a guide catheter system 600 may include a guide catheter 601 having a shaft 610 and a hub assembly 604 disposed at the proximal end of the shaft 610. The shaft 610 may include a proximal portion 603 having a first diameter, a terminal end portion 602 having a second, smaller diameter, a tapering transition 614 between the two, and a lumen 608 extending through the length of the shaft 610 and through the hub assembly 604. (The internal portion of the hub assembly 604 may be a lumen, a chamber or the like in fluid communication with the lumen 608 of the catheter shaft 610.) In some embodiments, the guide catheter system 600 may further include a guidewire 612 and/or a balloon catheter 606, as shown in FIG. 6. In some embodiments, the guide catheter system 600 may further include a suction device, such as suction tubing 633.

The outer profile of the shaft 610 is configured for advancement into a nasal cavity so that one or more devices may be advanced through the lumen 608 into a paranasal sinus. The tapering transition 614 is provided between the shaft proximal portion 603 and the distal portion 602 such that the distal portion 602 has a smaller cross-section than the proximal portion 603. In this way, a balloon catheter 606 can reside in the proximal portion 603 while suction forces are passed through the lumen 608, around the balloon catheter 606 structure. This configuration may be useful, for example, in advancing the guide catheter system 600 into a nostril of a patient with the balloon catheter 606 preloaded into the guide lumen 608 and allowing for suction during advancement and positioning of the guide catheter 601. Suction during advancement and positioning of the guide catheter 601 is advantageous because it allows for the removal of blood and mucus from the field in which the surgeon is working, thus facilitating visualization of the area and access to a paranasal sinus.

The shaft distal terminal portion 602 of the guide catheter 601 defines a specific curved profile intended to direct one or more devices advanced through the lumen 608 into a natural or manmade opening of a paranasal sinus. In one embodiment, the most distal tip 616 of the terminal end portion 602 is more flexible than the rest of the shaft 610. Accordingly, PEBAX is one contemplated material for the distal tip 616. An intermediate portion 618 of the shaft 610, which may include the tapering transition 614, may be made of a flexible material as well, but in one embodiment this material may be less flexible than material used to form the distal tip 616. For example, in one embodiment, the intermediate portion 618 may be formed of a nylon material. The proximal portion 603 of the shaft 610 proximal to this intermediate portion 618 may be formed of a more rigid material, such as but not limited to a more rigid polymer and/or a stainless steel hypotube 619.

One advantage of the flexible distal tip 616 is that it causes less trauma to soft mucosal tissue lining the nasal cavity as the guide catheter 601 is advanced, manipulated and retracted. For example, when the guide catheter 601 is advanced into the nasal cavity, the tip 616 may often contact the ethmoid bulla, and a flexible tip 616 will cause less trauma than a rigid one. In some embodiments, the distal tip 616 may also expand as a deflated balloon catheter 606 is drawn back into the guide catheter after a balloon dilation procedure has been performed. This expansion (or "give") may reduce the amount of force required to pull the balloon catheter 606 back into the guide catheter 601 after a procedure, thus making use of the balloon catheter 606/guide catheter 601 system easier. This also allows the distal tip 616 diameter to be made smaller than it otherwise would, which further reduces trauma during use and also facilitates positioning of the distal tip 616 at a desired location in the anatomy. The tip 616 may also be provided with an expandable radiopaque band to aid in tracking positioning during an interventional procedure as well as to maintain an atraumatic profile.

Further, the PEBAX distal tip 616 is shaped relative to the adjacent proximal portion 618 for navigation through and about nasal cavity structures. For instance, in one embodiment, the curved shape of the tip portion 616 facilitates navigating about an ucinate process, so that one or more devices may be navigated into a maxillary sinus. In one embodiment, a junction between the distal tip 616 and the adjacent intermediate portion 618 is slanted. This slanted connection increases the area of the distal tip 616 portion relative to the intermediate portion 618, thus increasing the area of the most flexible portion of the shaft 610, which enhances the prevention of soft tissue trauma. The angled shape of the terminal end portion 602 is retained in part due to the more rigid nylon of the intermediate portion 618 and its slanted junction with the distal tip portion 616.

In various alternative embodiments, a guide device such as the one described above and below may have any suitable angled configuration. For example, embodiments may be provided with different angles to facilitate access to maxillary, frontal, sphenoid and ethmoid paranasal sinuses. In various embodiments, the distal tip 616 may be angled relative to the rest of the shaft 610 at angles from approximately 0° to approximately 180°. In some embodiments, a combination of guide catheters 601 having different angled configurations may be provided, such as a set of guide catheters 601 having angles of 0°, 30°, 70° and 110°. A surgeon may then select a guide catheter 601 with a desired angle for accessing a given paranasal sinus. In various embodiments, any angle or guides with any combination of angles may be provided.

In various embodiments, the outer an inner diameters of the shaft 610, including the terminal end portion 602, tapering transition 614 and proximal portion 603, may have a number of different sizes, as long as the shaft 610 is configured for advancement into the nasal cavity. The terminal end portion 602 and distal tip portion 616, in particular, may be sized to facilitate positioning near an opening to a paranasal sinus. In one embodiment, for example, the distal tip 616 can have an inner diameter of approximately 0.093 inches. This diameter structure can extend longitudinally from the tip 616 and to the catheter portion distal to the taper 614 and can define a relatively long dimension. A tip envelop 620 of the terminal end portion 602, however, can assume a relatively short dimension so that it can more easily pass through nasal anatomy and thus potentially engaging less structure as it is inserted, for example, past a middle turbinate. The "tip envelope," for the purposes of this application, is defined as the length of a line drawn perpendicularly from the extreme distal end of the distal tip 616 to an oppositely facing surface of the straight portion of the terminal end portion 602, as shown in FIG. 7.

As shown in FIGS. 6 and 7, in one embodiment, the extreme distal end of the distal tip 616 may have a bevelled shaped. The bevelled shape also facilitates insertion and positioning relative to nasal cavity anatomy, such as directing the guide catheter 601 around the ucinate process to gain access to the maxillary sinus ostium. Moreover, the particular configuration of the beveled tip 616 permits an operator to view the opening of the tip when the device is placed within a nostril. This is due to the opening of the bevelled structure pointing back toward the operator. Such direct viewing of the opening of the tip 616 can aid in device manipulation and positioning.

In some embodiments, the lumen 608 in the terminal end portion 602 may have an inner diameter sized so that when the balloon catheter 606 is advanced within that portion of the lumen 608, suction is no longer possible, since an interference fit is created between the inner wall of the lumen 608 of the distal terminal end portion 602 and the outer surface of the balloon. In an alternative embodiment, it may still be possible to draw suction through the lumen 608 and around the balloon catheter 606, even in this advanced position, though the amount of suction force will be less when the balloon resides in the terminal end portion 602 compared with when it resides in the proximal shaft portion 603. Suction force may then be resumed again when the balloon catheter 606 is advanced distally beyond the tip 612 to perform an interventional procedure, although in some cases the primary use of suction may be during initial advancement and positioning of the guide catheter system 600 in the nasal cavity.

A proximal valve 624 is provided within the guide lumen 608 (or chamber of the hub 604). In one embodiment, the valve 624 forms a seal about the balloon catheter 606 to thereby facilitate the application of suction forces within the lumen 608. In one embodiment, the valve can be configured so that it also may form a seal around a guidewire 612. However, in an alternative embodiment, the valve does not form a seal about a guidewire 612, so that suction is only created when the balloon catheter 606 or another flexible device having a larger diameter than the guidewire 612 is positioned within the lumen 608.

The hub 604 of the guide catheter 601 further includes a vent 628 and a suction port 630. A most proximal portion is equipped with a flange 631 shaped for easy gripping by an operator. In one embodiment, for example, the flange 631 may be used by a surgeon to grip the guide catheter 601 like a syringe and advance the balloon catheter 606 through the guide catheter 601 with the same hand. In alternative embodiments, either standard or custom suction tubing 632 can be attached to the suction port 630 to create the desired suction force. Moreover, the suction port 630 is angled proximally so that a guidewire 612 advanced through the hub 604 will not exit the suction port 630.

The vent 628 is sized and positioned to accept an operator's finger, so that suction provided through the suction port 630 will be applied at the distal tip 616 of the guide catheter 601. In some embodiments, the vent 628 can define a short tubular path from an outer surface of the hub 604 to an inner wall of the hub 604 and can be directed proximally in a manner similar to the suction port 630, to prevent a guidewire 612 from passing through the vent 628. In one alternative embodiment, the vent 628 may also or alternatively be covered with a grate-like structure to prevent a guidewire 612 from passing therethrough.

With reference now to FIGS. 8-11, a method of using the guide catheter system 600 is described. Although FIGS. 8-11 show use of the guide catheter system 600 in accessing and treating a frontal paranasal sinus, this or other embodiments may be used to access and treat any of the other paranasal sinuses, including maxillary, sphenoid and ethmoid paranasal sinuses.

Figure 8:
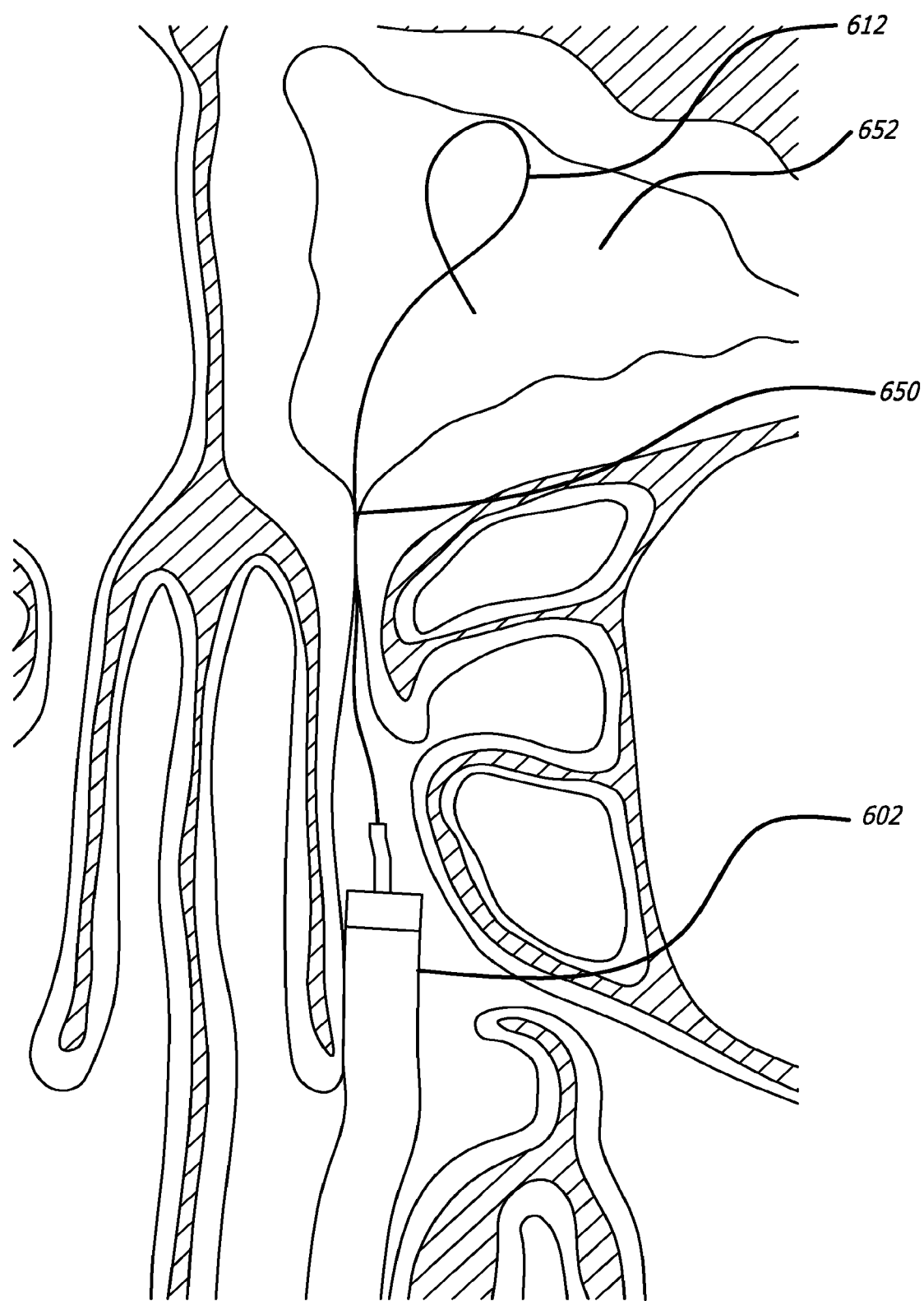
FIGS. 8 through 11 depict treating a sinus cavity with a guide catheter system.

Referring to FIG. 8, in one embodiment of the method, a guide catheter 601 is first advanced into a nasal cavity and positioned so that the terminal end portion 602 of the guide catheter 601 is located at or near an opening into a paranasal sinus. In the example shown in FIG. 8, the terminal end portion 602 is positioned near the frontal recess, which is a pathway leading to the frontal sinus ostium (the natural opening into the frontal sinus). The guide catheter 601 may be positioned in a desired location using an endoscope for visualization and/or fluoroscopy, however, in most cases an endoscope alone will suffice. In some embodiments, the guide catheter 601 is advanced into the nasal cavity with a guidewire 612 and/or a balloon catheter 606 preloaded into the guide catheter lumen 608. During advancement and/or positioning of the guide catheter 601, suction may be applied by applying suction force through a suction tube coupled with the hub apparatus 604 and by placing a thumb or other finger over the vent 628 to remove blood, mucus and/or other fluids from the area of the terminal end portion This use of suction will typically enhance a surgeon's ability to visualize the nasal cavity using an endoscope and thus facilitate location of a target paranasal sinus ostium.

Still referring to FIG. 8, once the guide catheter 601 is positioned in a desired location in the nasal cavity, the surgeon then advances the guidewire 612 out of the distal opening of the catheter 601 and through the natural ostium 650 of a paranasal sinus into the sinus cavity 652. In some embodiments, the guidewire 612 may be an illuminating guidewire. Such an illuminating guidewire may be used to create a transillumination spot on an external surface of the patient during and/or after advancement of the guidewire 612 to confirm that the distal end of the guidewire 612 has entered and resides in the desired paranasal sinus. (See, for example, U.S. patent application Ser. Nos. 11/522,497, issued as U.S. Pat. No. 7,559,925 on Jul. 14, 2009 and 11/803,695, issued as U.S. Pat. No. 9,554,691 on Jan. 31, 2017, the full disclosures of which are hereby incorporated by reference.) In other embodiments, a non-illuminating guidewire 612 may be used. In either the illuminating or non-illuminating guidewire embodiment, fluoroscopy may be used to visualize the guidewire 612 in the paranasal sinus for further confirmation of its location.

Figure 9:
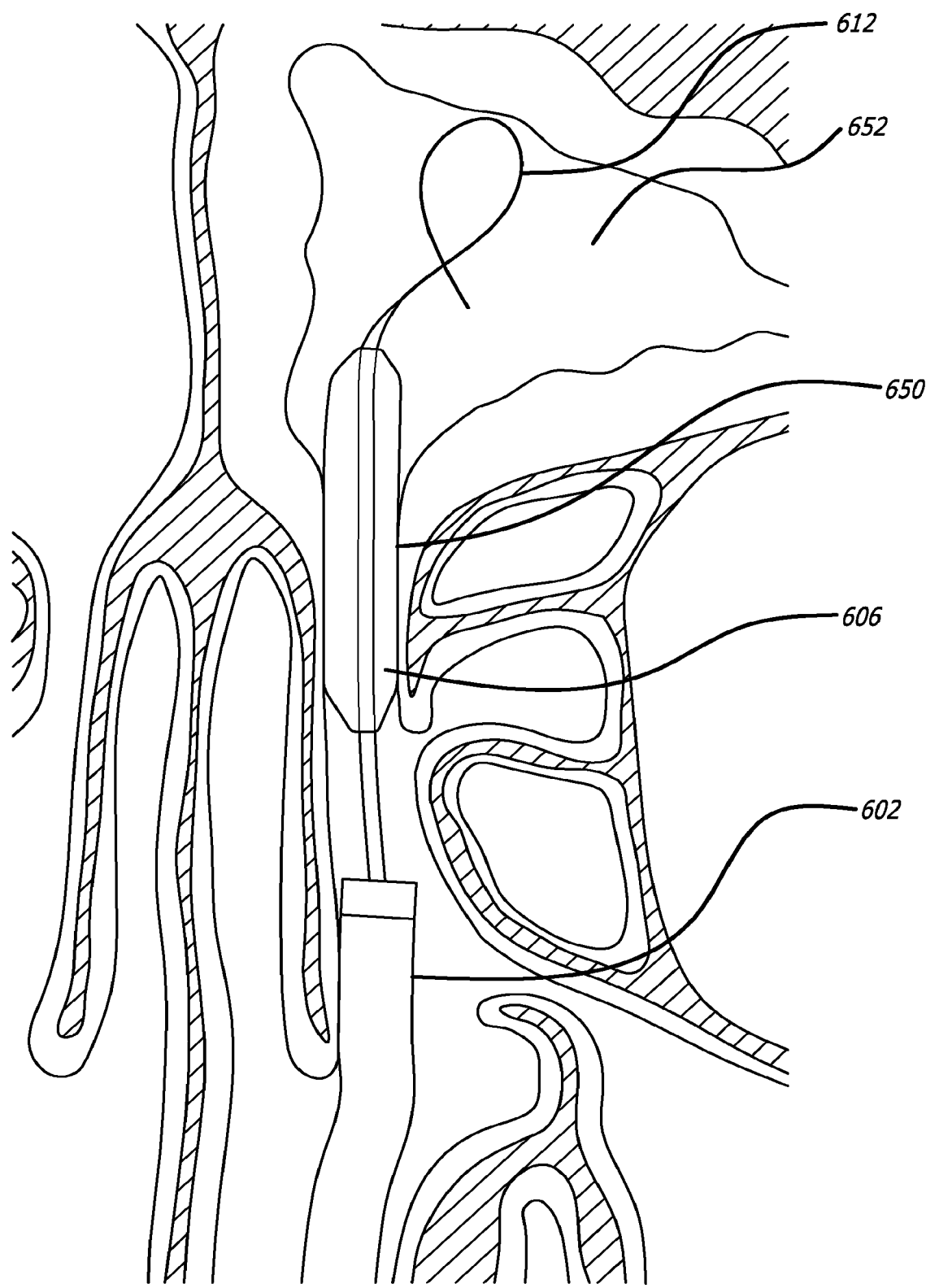

Next, as shown in FIG. 9, the balloon catheter 606 is advanced over the guidewire 612 and is positioned and then expanded within the paranasal sinus ostium 650. (In the case of the frontal sinus, as in these Figures, the balloon of the balloon catheter 606 may be positioned and inflated within the ostium, the frontal outflow tract or both.) An inflation device (not shown) is provided to inflate the balloon. Thereafter, the balloon catheter is deflated and withdrawn within the distal terminal end portion 602. In one embodiment, rather than immediately withdrawing the balloon catheter 606, instead the balloon may be repositioned and inflated again to further expand the ostium, expand a portion of the frontal sinus outflow tract and/or the like. Optionally, the balloon catheter 606 may be further withdrawn into the guide catheter 601, and a suction force may be applied to remove substances from the paranasal sinus cavity or outflow tract or from the nasal cavity.

Figure 10:
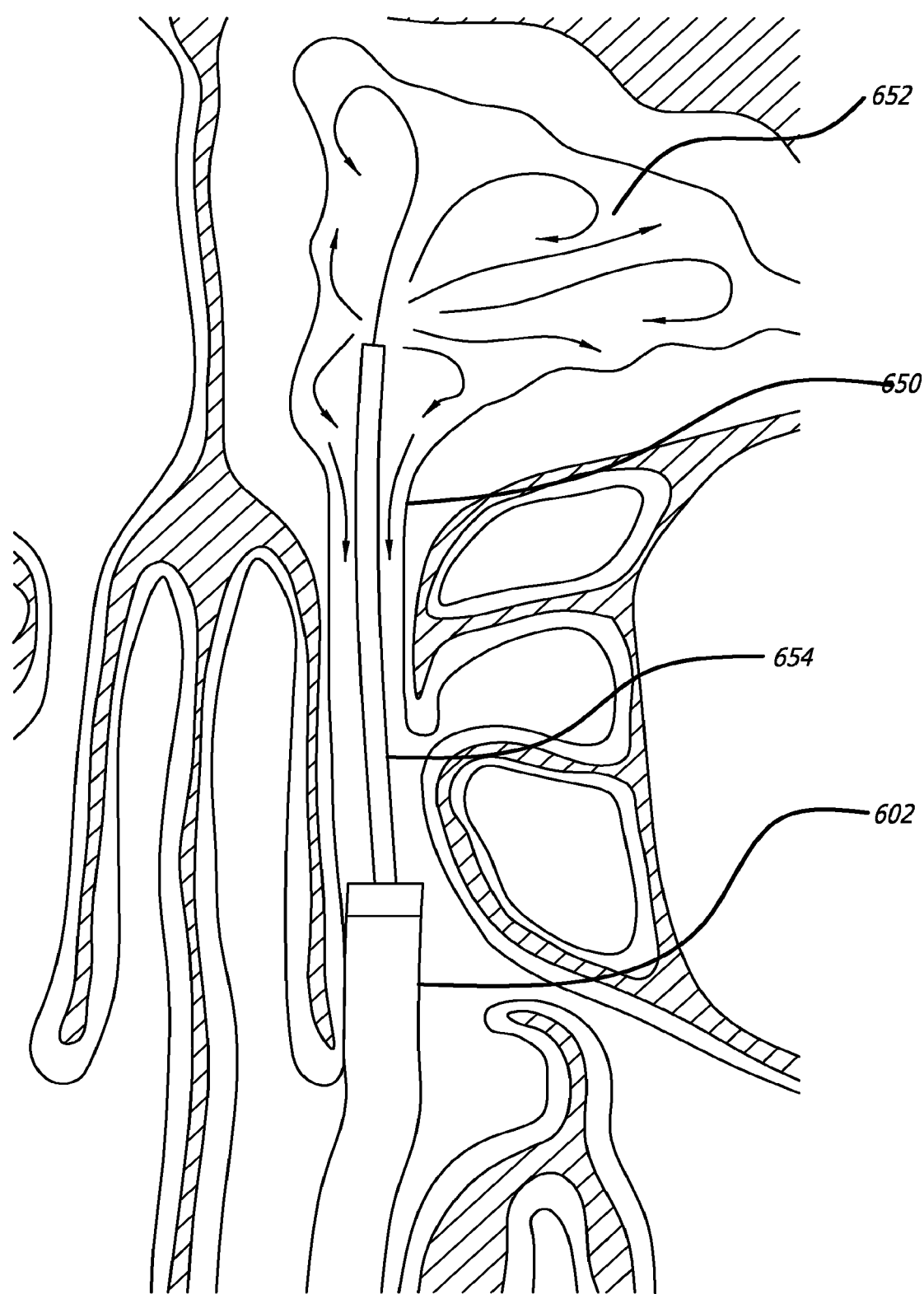

With reference now to FIG. 10, in an optional step, in some embodiments, the balloon catheter 606 may be removed from the patient via the guide catheter, and a flexible irrigation catheter 654 may then be passed through the guide catheter 601 (either over the guidewire 612 or without a guidewire, in alternative embodiments), into the paranasal sinus. Irrigation fluid 652, such as saline solution, may then be passed out of the irrigation catheter 654 to flush or irrigate the sinus. In some embodiments, the irrigation fluid 652 may simply be allowed to flow out of the sinus without applying suction force. In other embodiments, suction may be applied via the suction guide catheter 601 to assist in removal of the fluid 652.

Figure 11:
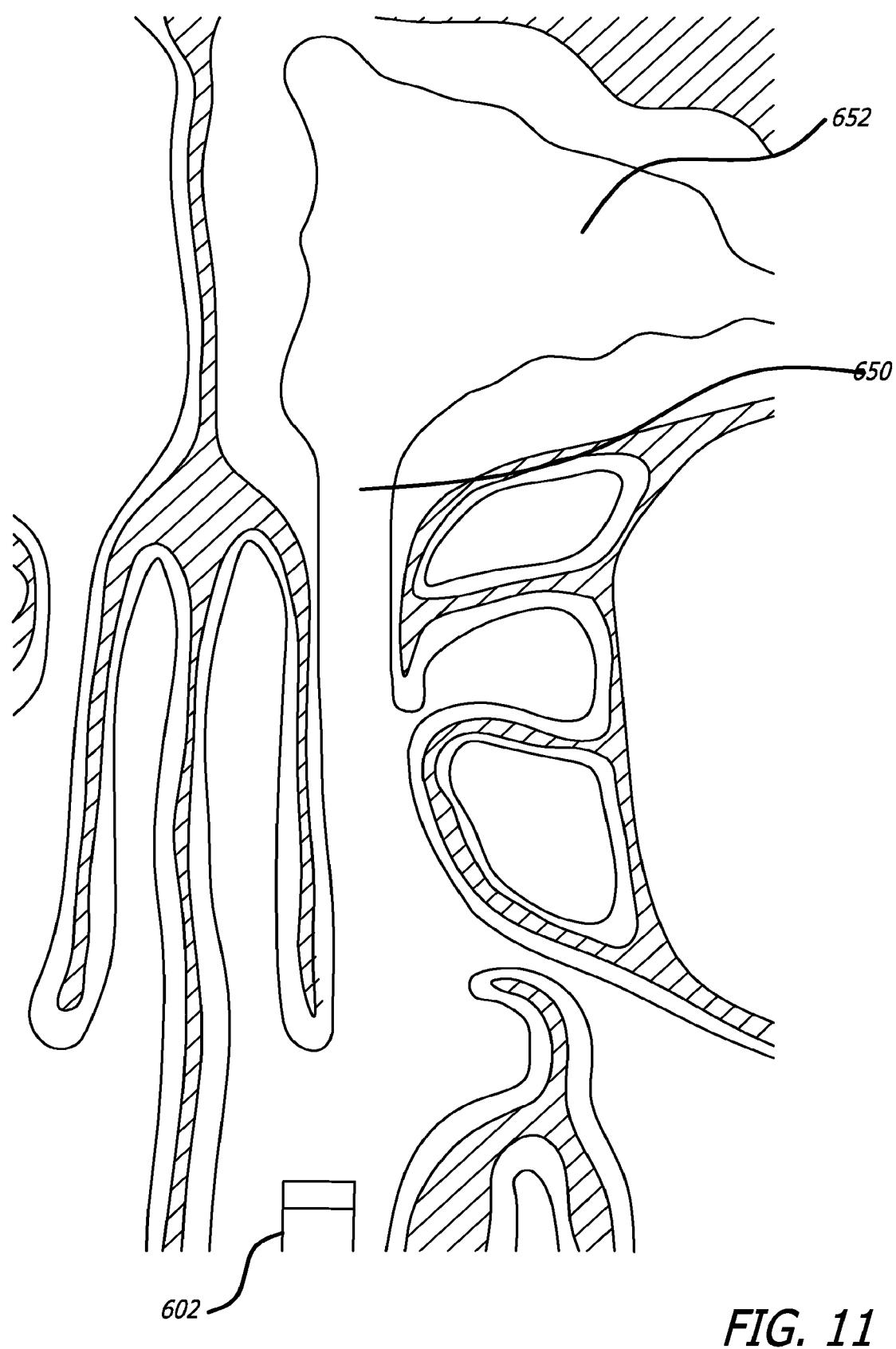

At the end of a procedure, as in FIG. 11, the guide catheter 601 and any remaining devices are removed from the patient. The ostium 650 is left in a dilated state, which ideally will facilitate normal drainage of the sinus and help treat the patient's sinusitis.

Figure 12:
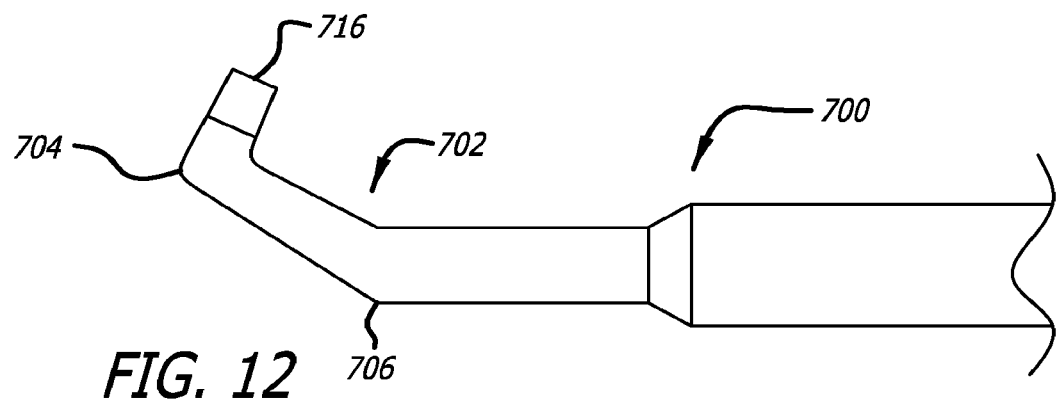
FIG. 12 shows an alternative distal portion for a guide catheter.

As shown in FIG. 12, an alternate approach to a guide catheter 700 may include a distal terminal end portion 702 which includes multiple turns or bends. A first bend 704 can be positioned distally with respect to a second bend 706, where the first bend 704 defines a smaller angle than the second bend 706. This "double-bend" configuration may facilitate insertion of the guide catheter 700 into a nostril in a tip-down orientation and then allow the catheter 700 to be rotated to position its distal tip 716 at or near a maxillary sinus ostium.

In other alternative embodiments, the terminal end portion 702 of a guide catheter 700 may be configured to facilitate other processes or manipulations within the nasal cavity. For example, in one embodiment the terminal end portion 702 may be configured to facilitate pushing an ucinate process (or other anatomy) out of the way during an interventional procedure while a distal tip 716 is positioned as desired relative to the treatment site. The "double-bend" approach shown in FIG. 12 may help lower insertion and retraction forces required to advance and retract a balloon catheter through the guide 700. For example, double bends of fifty and sixty degrees can be subjected to less such forces than a single bend of one hundred ten degrees.

Figure 13:
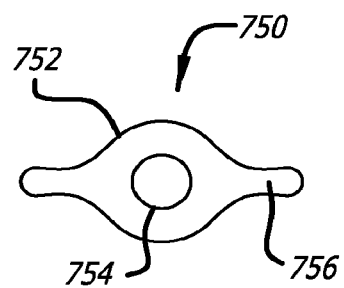
FIG. 13 depicts a cross-section of a distal terminal end portion of a guide catheter system.
Figure 14A:
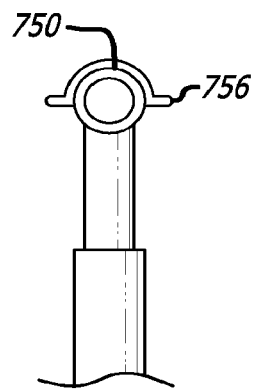
FIGS. 14A through 14C shows various views of a distal terminal end portion of a guide catheter system.
Figure 14B:
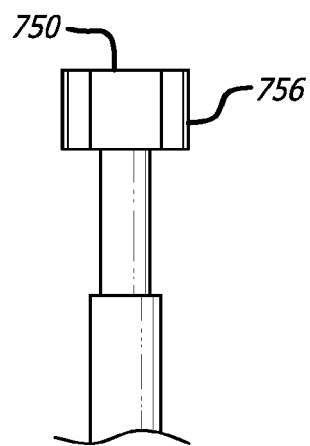
Figure 14C:
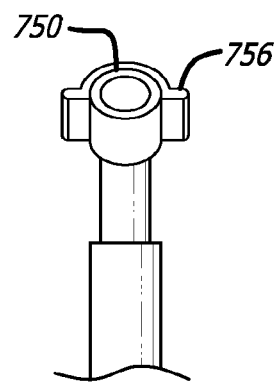

Turning now to FIGS. 13-23, a number of alternative embodiments of distal end configurations for guide catheters are shown. Each embodiment may have advantages in facilitating advancement and/or positioning of a guide catheter within a nasal cavity and/or advancement or retraction of a balloon catheter or other device(s) into and out of the guide catheter's distal end. As shown in FIG. 13, in one embodiment, a terminal end tip 750 of a guide catheter may embody an eye-shaped extrusion or molding 752, including a round inner diameter 754. Integrated wings 756 are provided to help gain access to and traverse nasal cavity anatomy. For example, the wings 756 may facilitate positioning the distal end of the guide catheter behind an uncinate process to access a maxillary sinus ostium. The wings 756 may allow a surgeon to tease the uncinate anteriorly, thus exposing an open pathway for guide access to the maxillary sinus ostium.

Some of the guide catheter distal ends in FIGS. 13-23 also include an oval cross-section. This oval shape may help to minimize the dimension of he guide in the orientation of anatomic restriction. Because the uncinate process can often be tight against the ethmoid bulla (in an anterior-posterior direction), the guide is ovalized such that the smaller dimension is oriented between the uncinate and the ethmoid bulla. Various embodiments may include such an oval cross-section with or without wings 756. The soft distal tip material of some embodiments of the guide catheters allow the cross-sectional shape of the guide tip to change relative to the forces it encounters. Therefore, a soft tip with a round cross-sectional shape may ovalize while it is being placed behind the uncinate, thereby reducing the force required to achieve a desired position.

Figure 15A:
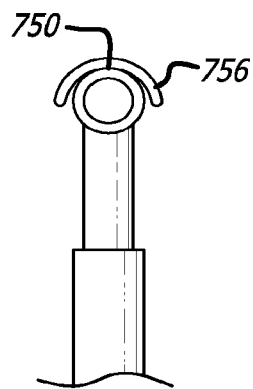
FIGS. 15A and 15B show a distal terminal end portion of an alternative guide catheter system.
Figure 15B:
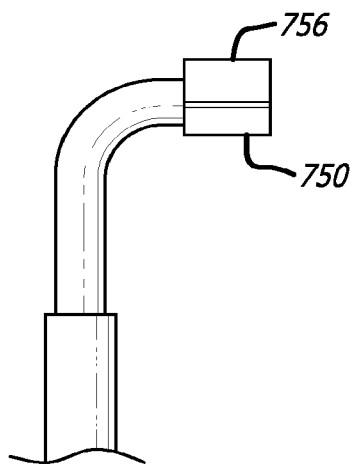
Figure 16:
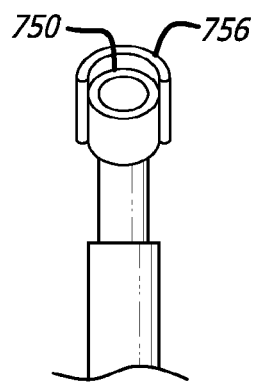
FIG. 16 shows another alternative terminal end portion of a guide catheter.

In other approaches, distal terminal end portions of a guide catheter can include flanged wings of various configurations. Wings can be positioned at the top, midline or bottom of a tip and the wing can be short, long, flat or curved. Also, the wings can be flared to form a single price of material and can be made of any suitable flexible or non-flexible material in various embodiments, such as but not limited to any number of metals or polymers, such as aluminum foil, stainless steel, hard plastic or soft plastic. In one specific approach (FIGS. 14A-14C), a distal terminal end portion 750 of a guide catheter can include wings 756 formed by aluminium foil. Such wings are again intended to facilitate navigation through sinus anatomy such as for the purpose of slipping behind an ucinate process. Similarly configured wings formed from PEBAX are shown in FIGS. 15A and 15B. Yet another approach to facilitating navigation is shown in FIG. 16 which depicts a hard plastic covering 758 formed about a portion the distal terminal end 750 of a guide catheter.

Figure 17A:
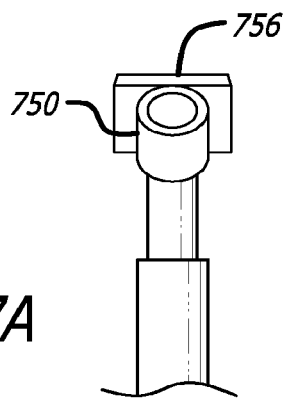
FIGS. 17A and 17B depict another approach to a terminal end portion.
Figure 17B:
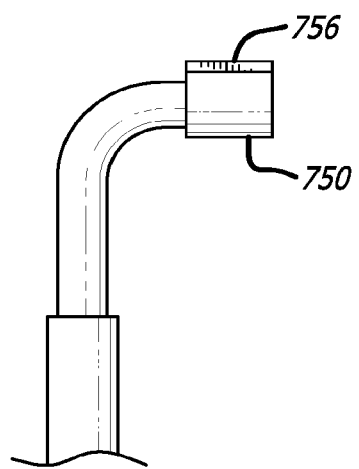
Figure 18A:
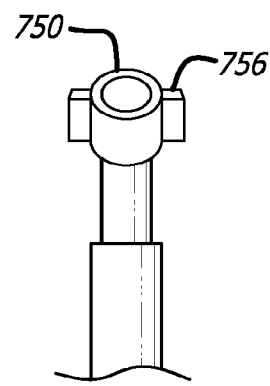
FIGS. 18A and 18B show a further approach to a terminal end.
Figure 18B:
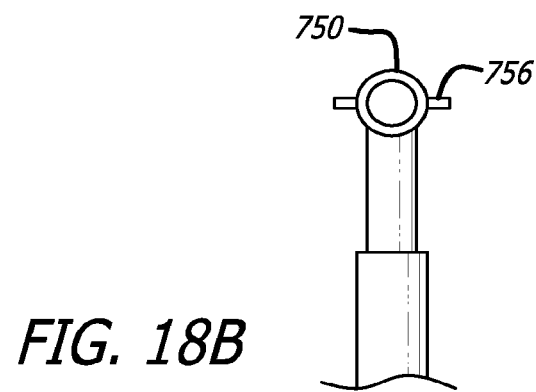
Figure 19A:
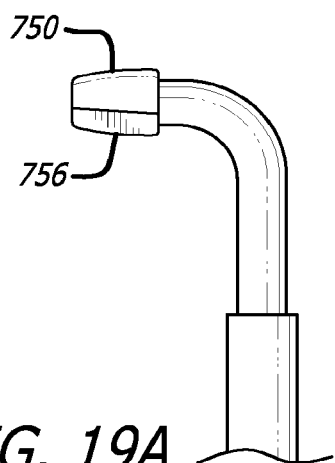
FIGS. 19A through 19D depict yet further terminal end portions for a guide catheter system.
Figure 19B:
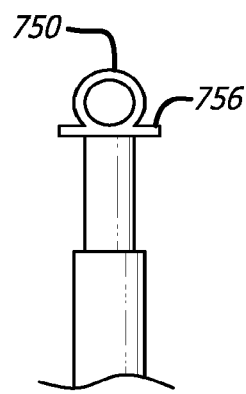
Figure 19C:
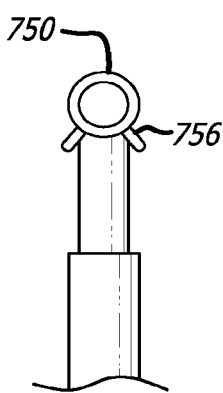
Figure 19D:
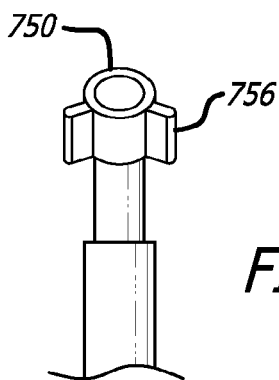
Figure 20A:
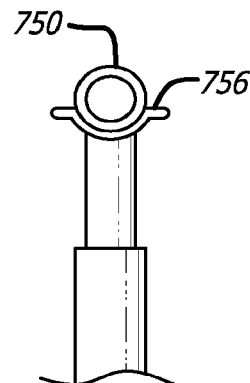
FIGS. 20A and 20B show views of an additional approach to a distal end portion of a guide catheter.
Figure 20B:
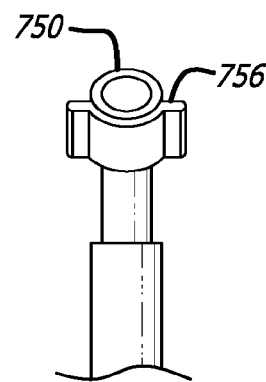
Figure 21A:
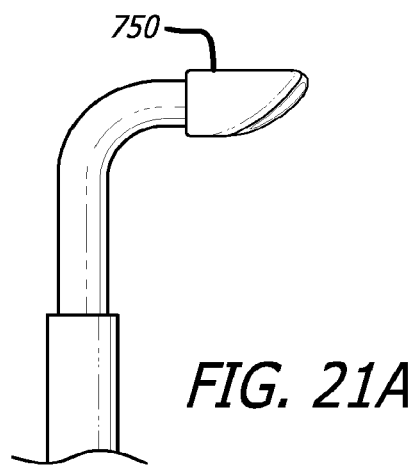
FIGS. 21A through 21C depict various views of a terminal end portion for guide catheter system which include an angled surface.
Figure 21B:
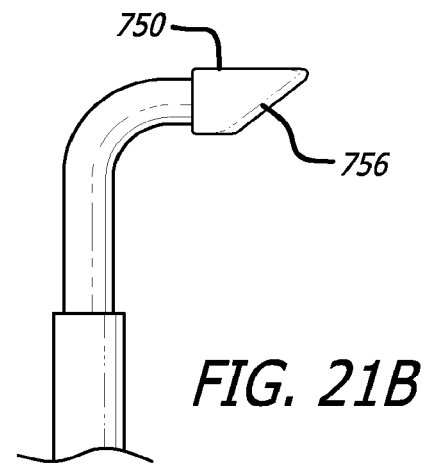
Figure 21C:
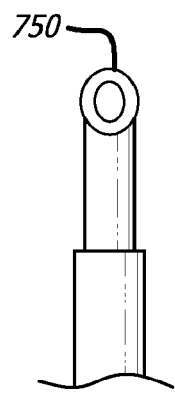
Figure 22A:
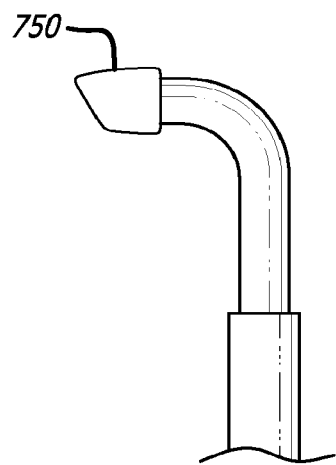
FIGS. 22A and 22B show another guide catheter system with an oval terminal end opening.
Figure 22B:
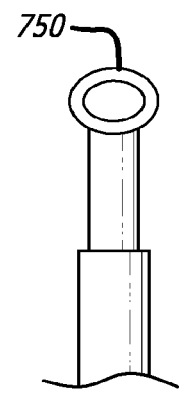
Figure 23:
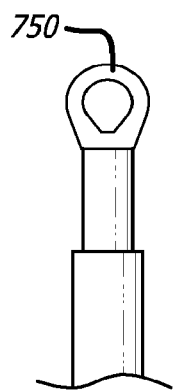
FIG. 23 depicts another alternative terminal end portion of a guide catheter system.

Moreover, as shown in FIGS. 17A-17B, navigating wings 757 can also be formed of a stainless steel bar configured across the terminal end generally perpendicular to a distal opening formed therein. Another approach to a PEBAX wing structure 756 is shown in FIGS. 18A and 18B. Yet further different approaches are depicted in FIGS. 19A-19D, 20A-20B, 21A-21C, 22A-22B and 23, respectively. Of particular note are the angled tip approach with underside wings 756 shown in FIG. 19A and the angle cut tips of FIGS. 21A-21C. Various shaped openings at the terminal ends of the guides are also contemplated such as those depicted in FIGS. 21A-21C, 22A-22B and 23.

As shown in FIGS. 24A-24C, various different approaches to a valve 624 for sealing a balloon catheter 606 within a guide catheter system are contemplated. In a first approach, a flat circular gasket 800 with a center sealing through hole 802 (FIG. 24A). Alternatively, a valve 810 defined by a through hole with a double taper 812 can be employed within a guide catheter system. Further, as shown in FIG. 24C, the valve 624 can embody a one-way valve 820 with internal flap structure 822.

Figure 25A:
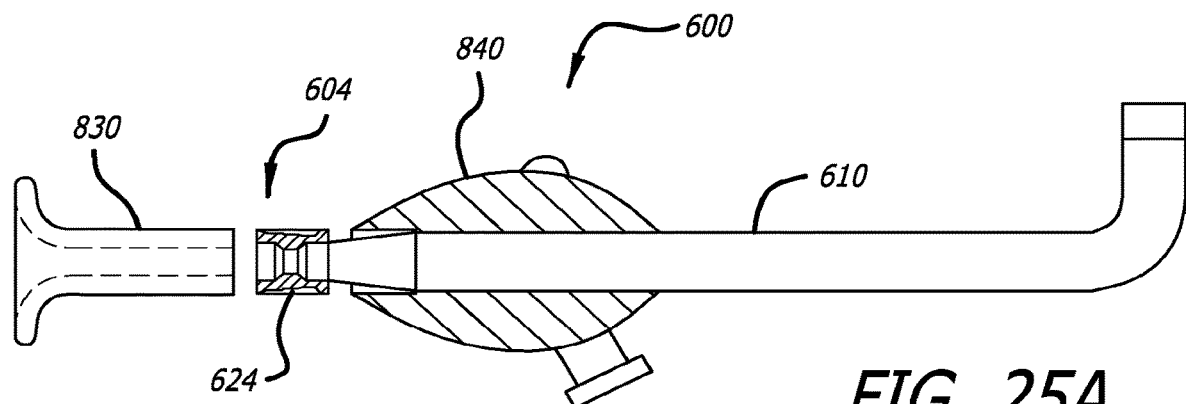
FIGS. 25A and 25B are partial cross-sectional views depicting alternative approaches to a hub assembly for a guide catheter.
Figure 25B:
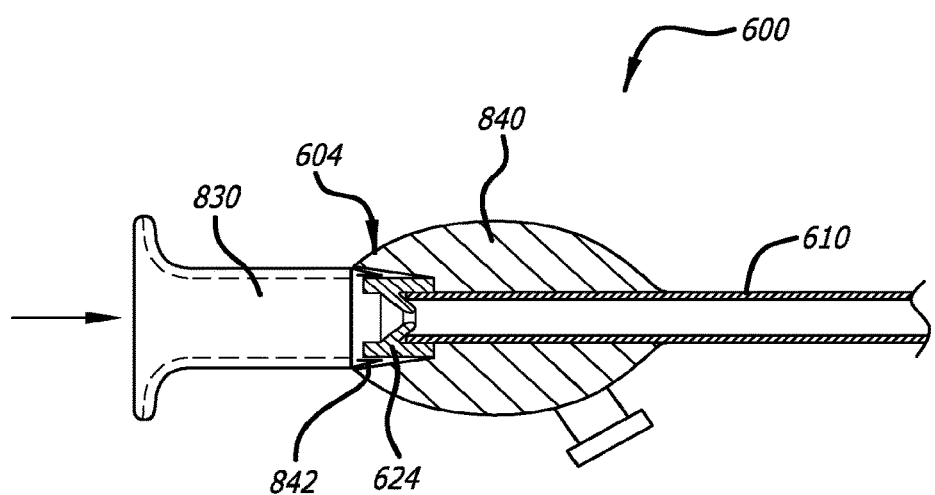

Turning now to FIGS. 25A and 25B, there are shown alternative approaches to a hub assembly 604 of a guide catheter system 600. By splitting the hub into first 830 and second 840 parts, an improved approach to attaching a valve seal 624 to a catheter shaft 610 is contemplated. In a first approach, the valve 624 is affixed to the shaft 610 and the two parts are positioned within the second part of the hub 604. The first part of the hub 830 is then inserted in the second part to complete the hub assembly. In an alternate approach (FIG. 25B), the valve 624 is captured in the second part 840 of the hub assembly and the end of the catheter shaft 610. The first part 830 of the hub is configured with flanges 842 which traps the valve 624 in place. Such approaches are intended for ease of assembly.

Figure 26:
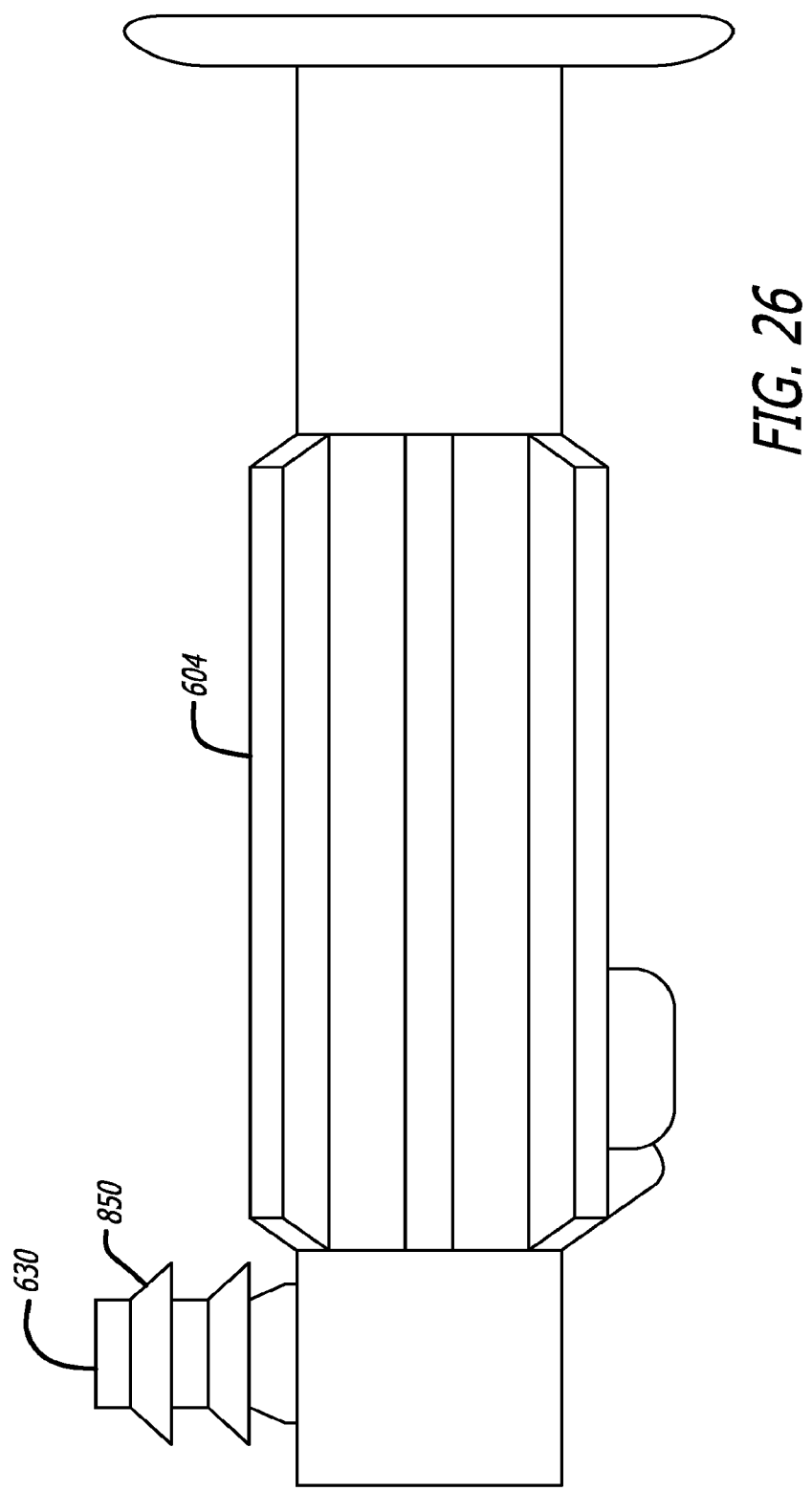
FIG. 26 depicts a guide catheter hub including a suction connection.

As shown in FIG. 26, the hub assembly 604 can further include a suction port 630 including barbs 850. The attachment for a suction tube must be one that allows for ease of attaching and removal, yet also from a tight seal to provide sufficient suction rates with little to no leakage. The barbs 850 facilitate such a desirable connection and also define a profile which does not interfere with an operator during use whether the suction feature is being employed or not.

Figure 27A:
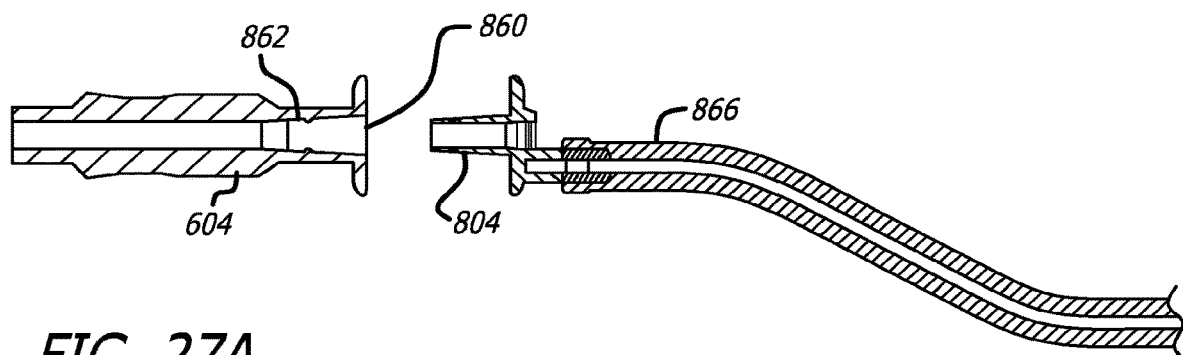
FIGS. 27A and 27B show a partial cross-sectional view of an auxiliary device connecting with a guide catheter hub.
Figure 27B:
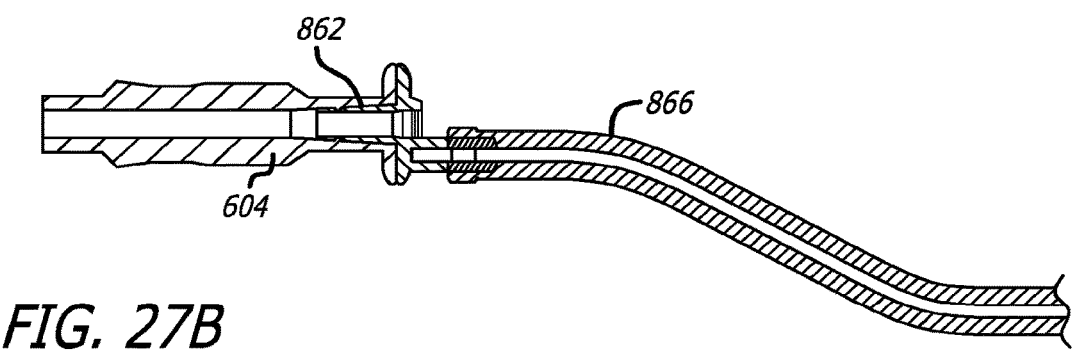

Additionally, as shown in FIGS. 27A and 27B, the hub assembly 604 can include a proximal opening 860 which can be provided for connecting the hub 604 to other devices. A ridge 862 can be formed within the opening 860 and can be sized and shaped to lockingly engage within a cut-out formed on an end of an auxiliary device 866. In this way, an audible click can be created by the engagement of the ridge 862 to thereby confirm a proper register of the hub 604 with auxiliary devices. With the cut-out 864 to thereby identify a full engagement of the ports. Additionally, some resistance is also provided between the ports to help avoid incidental release.

Although the present invention has been illustrated and described with respect to several preferred embodiments thereof, various changes, omissions and additions to the form and detail thereof, may be made therein, without departing from the spirit and scope of the invention.

What is claimed:

1. A method for advancing a flexible device into a paranasal sinus, the method comprising:
    (a) inserting a guide catheter into a head of a patient, wherein the flexible device is either preloaded into the guide catheter or advanced into the guide catheter during or after insertion of the guide catheter into the head of the patient;
    (b) moving a distal end of the guide catheter within the head of the patient such that the distal end is proximal relative to the paranasal sinus;
    (c) while the distal end of the guide catheter is proximal relative to the paranasal sinus, generating a suction force proximally through the guide catheter, around the flexible device, and within the head of the patient, via a suction source attached to the guide catheter, wherein the step of generating the suction force is performed while the flexible device is disposed within the guide catheter; and
    (d) advancing the flexible device out of the distal end of the guide catheter into the paranasal sinus.

2. The method of claim 1, wherein the act of moving the distal end of the guide catheter within the head of the patient occurs before advancing the flexible device out of the distal end of the guide catheter into the paranasal sinus.

3. The method of claim 1, further comprising retracting the flexible device through the distal end of the guide catheter.

4. The method of claim 3, further comprising inserting a flexible irrigation catheter through the distal end of the guide catheter and distributing irrigation fluid into the paranasal sinus of the patient via the flexible irrigation catheter.

5. The method of claim 4, further comprising generating the suction force while distributing irrigation fluid into the paranasal sinus of the patient.

6. The method of claim 1, wherein the distal end of the guide catheter defines a curved profile.

7. The method of claim 1, wherein the guide catheter comprises a shaft extending into the distal end, wherein the distal end is more flexible than the rest of the guide catheter.

8. The method of claim 1, wherein a hub is connected to a proximal end of the guide catheter.

9. The method of claim 8, wherein the hub is formed from two pieces.

10. The method of claim 8, wherein a valve is housed within the two pieces of the hub.

11. The method of claim 1, wherein the flexible device comprises a guidewire.

12. The method of claim 1, wherein the flexible device comprises a balloon catheter, wherein the method further comprises inflating the balloon catheter.

13. The method of claim 1, further comprising creating an artificial opening into the paranal sinus, wherein the flexible device is inserted through the artificial opening.

14. The method of claim 1, further comprising suctioning debris from the head of the patient.

15. A method for advancing a flexible device into a paranasal sinus, the method comprising:
    (a) inserting a distal end of a guide catheter into a head of a patient, wherein the flexible device is either preloaded into the guide catheter or advanced into the guide catheter via an instrument port during or after insertion of the guide catheter into the head of the patient;
    (b) moving the distal end of the guide catheter within the head of the patient to position the distal end of the guide catheter adjacent to the paranasal sinus;
    (c) generating a suction force proximally through the guide catheter, around the flexible device, and within the head of the patient via a suction source coupled to a suction port while the distal end of the guide catheter is adjacent to, yet spaced away from, the paranasal sinus; and (d) advancing the flexible device out of the distal end of the guide catheter within the paranasal sinus while the step of generating the suction force is being performed.

16. The method of claim 15, further comprising generating the suction force after advancing the flexible device out of the distal end of the guide catheter within the paranasal sinus.

17. The method of claim 15, wherein a seal is placed between the instrument port and the suction port.

18. The method of claim 15, further comprising irrigating the paranasal sinus after advancing the flexible device out of the distal end of the guide catheter.

19. The method of claim 15, wherein the flexible device comprises a balloon catheter, wherein advancing the flexible device out of the distal end of the guide catheter within the paranasal sinus further comprises inflating the balloon catheter is dilate an ostium.

20. A method for advancing a flexible device into a paranasal sinus, the method comprising:

(a) inserting a guide catheter into a head of a patient, wherein the flexible device is either preloaded into the guide catheter or advanced into the guide catheter during or after insertion of the guide catheter into the head of the patient;

(b) advancing a distal end of the guide catheter within the head of the patient and further positioning the distal end of the guide catheter proximally adjacent to the paranasal sinus such that the guide catheter is spaced away from the paranasal sinus;

(c) generating a suction force proximally through the guide catheter, around the flexible device, and within the head of the patient, via a suction source attached to the guide catheter, wherein the step of generating the suction force is performed while the distal end of the guide catheter is proximally adjacent to the paranasal sinus; and (d) advancing the flexible device out of the distal end of the guide catheter into the paranasal sinus.

* * * * *